(12) United States Patent
Gao et al.

(10) Patent No.: US 9,045,504 B2
(45) Date of Patent: Jun. 2, 2015

(54) LIGAND SYNTHESIS

(71) Applicants: Xiaoliang Gao, Calgary (CA); Darryl J. Morrison, Calgary (CA); Charles Ashton Garret Carter, Calgary (CA)

(72) Inventors: Xiaoliang Gao, Calgary (CA); Darryl J. Morrison, Calgary (CA); Charles Ashton Garret Carter, Calgary (CA)

(73) Assignee: Nova Chemicals (International) S.A., Fribourg (CH)

( * ) Notice: Subject to any disclaimer, the term of this patent is extended or adjusted under 35 U.S.C. 154(b) by 11 days.

(21) Appl. No.: 13/870,518

(22) Filed: Apr. 25, 2013

(65) Prior Publication Data

US 2013/0310590 A1 Nov. 21, 2013

(30) Foreign Application Priority Data

May 17, 2012 (CA) ...................................... 2777461

(51) Int. Cl.
  *C07F 7/08* (2006.01)
  *C07F 7/16* (2006.01)
(52) U.S. Cl.
  CPC ................. *C07F 7/16* (2013.01); *C07F 7/0827* (2013.01); *C07F 7/083* (2013.01)

(58) Field of Classification Search
  USPC ........................... 556/478, 489; 502/157, 158
  See application file for complete search history.

(56) References Cited

U.S. PATENT DOCUMENTS

| | | | |
|---|---|---|---|
| 7,064,096 B1 | 6/2006 | Hoang et al. | |
| 7,321,015 B2 | 1/2008 | Hoang et al. | |
| 7,323,523 B2 | 1/2008 | Hoang et al. | |
| 7,531,602 B2 * | 5/2009 | Hoang et al. ................. | 525/240 |

OTHER PUBLICATIONS

A. B. Pangborn, M.A. Giardello, R. H. Grubbs, R. K. Rosen and F. J. Timmers, Safe and convenient procedure for solvent purification, Organometallics 1996, 15, p. 1518-1520.

* cited by examiner

*Primary Examiner* — Sudhakar Katakam
*Assistant Examiner* — Pancham Bakshi
(74) *Attorney, Agent, or Firm* — Kenneth H Johnson

(57) ABSTRACT

Compounds 1,3,4-$(SiMe_3)(C_6F_5)$(alkyl)$C_5H_3$ are made using a simplified synthetic strategy which is readily scalable. On reaction with a suitable transition metal species, a 1,3,4-$(SiMe_3)(C_6F_5)$(alkyl)$C_5H_3$ molecule provides an organotransition metal complex comprising a 1,2-$(C_6F_5)$(alkyl) substituted cyclopentadienyl ligand, which is active toward olefin polymerization.

38 Claims, No Drawings

US 9,045,504 B2

LIGAND SYNTHESIS

FIELD OF THE INVENTION

Compounds with the formula 1,3,4-$(SiMe_3)(C_6F_5)(R)C_5H_3$ where R is a primary or a secondary alkyl group (which may optionally be further substituted with one or more heteroatom or heteroatom containing group) are made using a simple, scalable synthetic method. The compounds 1,3,4-$(SiMe_3)(C_6F_5)(R)C_5H_3$ are useful ligand precursors which can be used to provide organotransition metal complexes comprising a 1,2-$(C_6F_5)(R)$ substituted cyclopentadienyl ligand, and which are active toward olefin polymerization.

BACKGROUND OF THE INVENTION

The identification of new and improved synthetic methods for making ligand precursors which are used to construct highly active polymerization catalysts is of importance to the polymer industry.

The known ligand precursor 1,3,4-$(SiMe_3)(C_6F_5)$(n-alkyl)$C_5H_3$ has been successfully employed in the synthesis of phosphinimine complexes which are highly active olefin polymerization catalysts.

Previously published methods for making the ligand precursor 1,3,4-$(SiMe_3)(C_6F_5)(R)C_5H_3$ (where R is n-propyl, n-butyl, or n-hexyl), although effective in terms of overall yield, involved the isolation of intermediates and required the use of several work-up steps, as well as time consuming filtrations steps. Multiple reaction vessels were also required. See for example U.S. Pat. Nos. 7,531,602, 7,064,096, 7,321,015 and 7,323,523.

SUMMARY OF THE INVENTION

We now disclose that, the ligand precursor 1,3,4-$(SiMe_3)(C_6F_5)(R)C_5H_3$ where R is a primary or secondary alkyl group, can be synthesized in good overall yield and purity (optionally using a single reaction vessel) without isolating process intermediates and without time consuming filtrations steps. The new method, which employs fewer process steps than the prior art method, is readily scalable to a commercial scale, without negative impact to product yield or purity. We have also found an aqueous product work-up which minimizes product decomposition and avoids filtration of finely divided inorganic salts. As a result, synthetic time and process economics for the production of the ligand precursor at scale are improved.

Provided is a method for making the compound 1,3,4-$(SiMe_3)(C_6F_5)(R)C_5H_3$ without isolating intermediates, said method comprising the following steps:

Step 1) in the presence of an ethereal solvent, combining perfluorobenzene $C_6F_6$, a metal cyclopentadienide [$M^1$][$C_5H_5$] and a first base $M^2B^1$ to form a first reaction mixture comprising [$M^1/M^2$][$(C_6F_5)C_5H_4$];

Step 2) combining at least 2 molar equivalents of $ClSiMe_3$ with said first reaction mixture to give a second reaction mixture comprising 1,3-$(SiMe_3)(C_6F_5)C_5H_4$;

Step 3) combining a second base $M^3B^2$ with said second reaction mixture to give a third reaction mixture comprising [$M^1/M^2/M^3$][1,3-$(SiMe_3)(C_6F_5)C_5H_3$];

Step 4) combining a compound RX with said third mixture to give a fourth reaction mixture comprising 1,3,4-$(SiMe_3)(C_6F_5)(R)C_5H_3$;

wherein $M^1$, $M^2$, $M^3$ are the same or different metal selected from the group consisting of $Li^+$, $Na^+$ and $K^+$; $B^1$ and $B^2$ are the same or different bases selected from the group consisting of hydride, alkylide, amide and alkoxide; R is a primary or secondary alkyl group which may optionally be substituted by one or more heteroatom or heteroatom group; and X is a halide group or a sulfonate group.

Provided is a method for making the compound 1,3,4-$(SiMe_3)(C_6F_5)(R)C_5H_3$ in a single reaction vessel without isolating intermediates, said method comprising the following steps:

Step 1) in the presence of an ethereal solvent, combining perfluorobenzene $C_6F_6$, a metal cyclopentadienide [$M^1$][$C_5H_5$] and a first base $M^2B^1$ to form a first reaction mixture comprising [$M^1/M^2$][$(C_6F_5)C_5H_4$];

Step 2) adding at least 2 equivalents of $ClSiMe_3$ to said first reaction mixture to give a second reaction mixture comprising 1,3-$(SiMe_3)(C_6F_5)C_5H_4$;

Step 3) adding a second base $M^3B^2$ to said second reaction mixture to give a third reaction mixture comprising [$M^1/M^2/M^3$][1,3-$(SiMe_3)(C_6F_5)C_5H_3$];

Step 4) adding a compound RX to said third mixture to give a fourth reaction mixture comprising 1,3,4-$(SiMe_3)(C_6F_5)(R)C_5H_3$;

wherein $M^1$, $M^2$, $M^3$ are the same or different metal selected from the group consisting of $Li^+$, $Na^+$ and $K^+$; $B^1$ and $B^2$ are the same or different bases selected from the group consisting of hydride, alkylide, amide and alkoxide; R is a primary or secondary alkyl group which may optionally be substituted by one or more heteroatom or heteroatom group; and X is a halide group or a sulfonate group.

The improved ligand synthesis provided by the current invention may also comprise one or more of the following embodiments:

In an embodiment of the invention, approximately equimolar amounts of $C_6F_6$, [Na][$C_5H_5$] and NaH are combined in step 1.

In an embodiment of the invention, $C_6F_6$ is combined with approximately 2 molar equivalents of [Na][$C_5H_5$] in step 1.

In an embodiment of the invention, $C_6F_6$ is added slowly over at least 30 min to approximately 2 molar equivalents of [Na][$C_5H_5$] in step 1.

In an embodiment of the invention, $C_6F_6$ is added slowly over at least 30 min to an approximately equimolar amount of a 1:1 mixture of [Na][$C_5H_5$] and NaH in step 1.

In an embodiment of the invention, approximately 2 molar equivalents of $ClSiMe_3$ are combined with the first reaction mixture in step 2.

In an embodiment of the invention, the first reaction mixture is added to least 2 molar equivalents of $ClSiMe_3$ in step 2.

In an embodiment of the invention, at least 2 molar equivalents of $ClSiMe_3$ are added to the first reaction mixture in step 2.

In an embodiment of the invention, at least 2 molar equivalents of $ClSiMe_3$ are added in less than 5 min to the first reaction mixture in step 2.

In an embodiment of the invention, approximately 1 molar equivalent of the second base $M^3B^2$ is combined with the second reaction mixture in step 3.

In an embodiment of the invention, approximately 1 molar equivalent of the second base $M^3B^2$ is added in step 3.

In an embodiment of the invention, the second base $M^3B^2$ is a sodium alkoxide compound or a potassium alkoxide compound.

In an embodiment of the invention, the second base $M^3B^2$ is [Na][OtBu].

In an embodiment of the invention, the second base $M^3B^2$ is [K][OtBu].

In an embodiment of the invention, the second base $M^3B^2$ is a metal alkylide reagent.

In an embodiment of the invention, the second base $M^3B^2$ is n-butyllithium.

In an embodiment of the invention, the second base $M^3B^2$ is $[Na][C_5H_5]$.

In an embodiment of the invention, at least 1 molar equivalent of RX is combined with the third reaction mixture comprising $[M^1/M^2/M^3][1,3-(SiMe_3)(C_6F_5)C_5H_3]$ in step 4.

In an embodiment of the invention, approximately 1.5 molar equivalents of RX are combined with the third reaction mixture comprising $[M^1/M^2/M^3][1,3-(SiMe_3)(C_6F_5)C_5H_3]$ in step 4.

In an embodiment of the invention, the compound RX is added to the third reaction mixture comprising $[M^1/M^2/M^3][1,3-(SiMe_3)(C_6F_5)C_5H_3]$ in step 4 in a molar ratio of greater than 1:1.

In an embodiment of the invention, the compound RX is added to the third reaction mixture comprising $[M^1/M^2/M^3][1,3-(SiMe_3)(C_6F_5)C_5H_3]$ in step 4 in a molar ratio of about 1.5:1.

In an embodiment of the invention, the compound RX is a primary alkyl halide in which R is a primary alkyl group which may optionally be substituted by one or more heteroatom or heteroatom group and X is Cl, Br or I.

In an embodiment of the invention, the compound RX is a primary alkyl halide in which R is a primary alkyl group which may optionally be substituted by one or more fluorine atom and X is Cl, Br or I.

In an embodiment of the invention, the compound RX is a primary alkyl halide which is selected from the group consisting of n-propyl bromide, n-butyl bromide, n-pentyl bromide, n-hexyl bromide, benzyl bromide and perfluorophenylbenzyl bromide.

In an embodiment of the invention, the ethereal solvent is selected from the group consisting of diethyl ether, diisopropyl ether, di-n-butyl ether, di-n-propyl ether, methyl t-butyl ether, diphenyl ether, tetrahydrofuran, 2-methyl-tetrahydrofuran or a mixture thereof.

In an embodiment of the invention, the ethereal solvent is selected from diethyl ether, tetrahydrofuran or a mixture thereof.

In an embodiment of the invention, the ethereal solvent is tetrahydrofuran.

In an embodiment of the invention, the ethereal solvent has less than 20 ppm of water.

In an embodiment of the invention, the compound 1,3,4-$(SiMe_3)(C_6F_5)(R)C_5H_3$ is prepared at a 500 mmol scale or higher.

In an embodiment of the invention, steps 1-4 are carried out in a single reaction vessel.

In an embodiment of the invention, a method for making the compound 1,3,4-$(SiMe_3)(C_6F_5)(R)C_5H_3$ further comprises the following steps:
a) removing volatiles from the fourth reaction mixture under vacuum to give a first residue comprising 1,3,4-$(SiMe_3)(C_6F_5)(R)C_5H_3$;
b) diluting the first residue with a hydrocarbon solvent to give a hydrocarbon solution comprising 1,3,4-$(SiMe_3)(C_6F_5)(R)C_5H_3$;
c) extracting the hydrocarbon solution with a mildly acidic aqueous solution to at least partially remove inorganic salts from the hydrocarbon solution comprising 1,3,4-$(SiMe_3)(C_6F_5)(R)C_5H_3$;
d) removing volatiles from the hydrocarbon solution under vacuum to give a crude product comprising 1,3,4-$(SiMe_3)(C_6F_5)(R)C_5H_3$ as the majority species by weight.

In an embodiment of the invention, a method for making the compound 1,3,4-$(SiMe_3)(C_6F_5)(R)C_5H_3$ further comprises the following steps:
a) diluting the fourth mixture with a hydrocarbon solvent to give a product mixture comprising 1,3,4-$(SiMe_3)(C_6F_5)(R)C_5H_3$;
b) extracting the product mixture with a mildly acidic aqueous solution to at least partially remove inorganic salts from the product mixture comprising 1,3,4-$(SiMe_3)(C_6F_5)(R)C_5H_3$,
c) removing volatiles from the product mixture under vacuum to give a crude product comprising 1,3,4-$(SiMe_3)(C_6F_5)(R)C_5H_3$ as the majority species by weight.

In an embodiment of the invention, a method for making the compound 1,3,4-$(SiMe_3)(C_6F_5)(R)C_5H_3$ further comprises the following steps:
a) removing volatiles from the fourth reaction mixture under vacuum to give a first residue comprising 1,3,4-$(SiMe_3)(C_6F_5)(R)C_5H_3$;
b) extracting the first residue with a hydrocarbon solvent to give a hydrocarbon solution comprising 1,3,4-$(SiMe_3)(C_6F_5)(R)C_5H_3$;
c) filtering the hydrocarbon solution comprising 1,3,4-$(SiMe_3)(C_6F_5)(R)C_5H_3$ to give a filtrate comprising 1,3,4-$(SiMe_3)(C_6F_5)(R)C_5H_3$;
d) removing volatiles from the filtrate to give a crude product comprising 1,3,4-$(SiMe_3)(C_6F_5)(R)C_5H_3$ as the majority species by weight.

In an embodiment of the invention, a method for making the compound 1,3,4-$(SiMe_3)(C_6F_5)(R)C_5H_3$ further comprises vacuum distillation of a crude product to give a distillate comprising 1,3,4-$(SiMe_3)(C_6F_5)(R)C_5H_3$ in greater than 40% purity by mole.

DETAILED DESCRIPTION OF PREFERRED EMBODIMENTS

The present invention is directed to new methods for synthesizing a useful ligand precursor compound. The new methods eliminate the need to isolate reaction intermediates in order to obtain acceptable yields. When the ligand precursor is metallated by reaction with a suitable group 4 transition metal species, an active polymerization catalyst is obtained. Method for the Preparation of 1,3,4-$(SiMe_3)(C_6F_5)(R)C_5H_3$.

The invention provides an improved method for making the compound 1,3,4-$(SiMe_3)(C_6F_5)(R)C_5H_3$, where R is a primary or secondary alkyl group (which may be substituted by one or more heteroatom or heteroatom containing group), and which can be employed as a ligand precursor in metallation reactions (e.g. the reaction of a transition metal compound with an ligand precursor, typically an organic compound, to form a metal complex having at least one metal-ligand bond).

In the present invention, the term "cyclopentadienide" refers to the anionic unsubstituted five carbon ring ($C_5H_5^-$) having the structure (I).

(I)

In the present invention the stoichiometry is defined relative to the amount of perfluorobenzene ($C_6F_6$) used for the synthesis of 1,3,4-$(SiMe_3)(C_6F_5)(R)C_5H_3$. Hence the terms "molar equivalent", "molar ratio" and similar such terms define the mole ratio or amount of a compound relative to the number of moles of perfluorobenzene ($C_6F_6$) employed in step 1.

In the present invention, a "hydrocarbon solvent" is any hydrocarbon solvent found to be suitable for dissolving or suspending the compounds of the present invention and includes by way of non-limiting example, pentane, cyclopentane, hexane, isohexane, cyclohexane, heptane, benzene and toluene, or a combination thereof.

In the present invention the term "leaving group" is any group which can be displaced or replaced by a suitable nucleophile, such as a cyclopentadienide anion or a singly or multiply substituted cyclopentadienide anion. Suitable leaving groups are well known in the art and include for example halides such a chloride, bromide and iodide, or sulfonate groups such as a mesylate or tosylate.

Step 1. In the first synthetic step, approximately equimolar amounts of perfluorobenzene ($C_6F_6$), a metal cyclopentadienide reagent $[M^1][C_5H_5]$ and a first base $M^2B^1$ are combined in an ethereal solvent to give a first reaction mixture which comprises a compound $[M^1/M^2][(C_6F_5)C_5H_4]$ which has the structure (II),

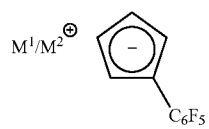

(II)

where $M^1/M^2$ indicates that mixed metal salts of the anion $(C_6F_5)C_5H_4^-$ may be present when $M^1 \neq M^2$, although $M^1$ may also be the same metal as $M^2$ ($M^1=M^2$).

The cyclopentadienide reagent $[M^1][C_5H_5]$ can have any suitable metal cation such as for example, $Na^+$, $Li^+$, or $K^+$. Other sources of the cyclopentadienide anion such as for example a cyclopentadienyl Grignard reagent $X'Mg(C_5H_5)$ where $X'$ is a halide are also contemplated for use in step 1 of the current invention.

The base $M^2B^1$ is preferably a base selected from the group consisting of metal hydride, metal alkylide (including cyclic alkylides, or aromatic cyclic alkylides such as those based on the cyclopentadienide anion), metal amide and metal alkoxide bases, where $M^2$ is preferably selected from the group consisting of $Li^+$, $Na^+$, and $K^+$.

In an embodiment of the invention, the base $M^2B^1$ is an alkyl lithium compound.

In an embodiment of the invention, the base $M^2B^1$ is a metal amide $[M^2][NH_2]$ compound were $M^2$ is $Li^+$, $Na^+$ or $K^+$.

In an embodiment of the invention, the base $M^2B^1$ is a sodium amide $NaNH_2$.

In an embodiment of the invention, the base $M^2B^1$ is a metal cyclopentadienide compound $[M^2][C_5H_5]$ where $M^2$ is $Li^+$, $Na^+$ or $K^+$.

In embodiments of the invention, the base $M^2B^1$ is sodium hydride (NaH) or sodium cyclopentadienide ($[Na][C_5H_5]$).

In embodiments of the invention, the base $M^2B^1$ may be a non-nucleophilic sterically encumbered metal amide such as those derived from 2,2,6,6-tetramethylpiperidine (e.g. lithium or sodium 2,2,6,6-tetramethylpiperidide), hexamethyldisilazane (e.g. lithium or sodium bis(trimethylsilyl)amide) and the like.

In embodiments of the invention, step 1 provides $[M^1/M^2][(C_6F_5)C_5H_4]$ in at least about 50% yield, or in at least about 60% yield, or in at least about 70% yield by mole percent.

The ethereal solvent used in the invention can be selected from a range of ethereal solvents including but not limited to diethyl ether, diisopropyl ether, di-n-butyl ether, di-n-propyl ether, methyl t-butyl ether, diphenyl ether, tetrahydrofuran, 2-methyltetrahydrofuran or any combination thereof.

In an embodiment of the invention, step 1 is carried out in diethyl ether.

In an embodiment of the invention, step 1 is carried out in tetrahydrofuran (THF).

The order of addition of the reagents in step 1 is not especially important, but by way of non-limiting example, a solution of $C_6F_6$ in an ethereal solvent is added to a $[M^1][C_5H_5]$:$M^2B^1$ (1:1 molar ratio) mixture in an ethereal solvent. In another embodiment, $C_6F_6$ and $[M^1][C_5H_5]$ are combined in an ethereal solvent followed by addition of the base $M^2B^1$. In an embodiment of the invention, $M^2B^1$ is also a $[M^1][C_5H_5]$ compound and $C_6F_6$ is combined with approximately two molar equivalents of $[M^1][C_5H_5]$ in an ethereal solvent.

The reaction time for step 1 is not specifically defined and will depend on various factors such as the reaction scale, temperature, solvent choice, reagent concentration and the like. By way on non-limiting example only, in an embodiment of the invention, it is preferable to add the $C_6F_6$ to $[M^1][C_5H_5]$ and a base $M^2B^1$ slowly. For example the $C_6F_6$ may be added to $[M^1][C_5H_5]$ and a base $M^2B^1$ slowly over at least a 15 min period, or slowly over at least a 30 min period, or slowly over at least a 60 min period.

The reaction temperature used for step 1 is not specifically defined and will depend on various factors such as the reaction scale, solvent choice, reagent concentration and the like. In an embodiment of the invention, step 1 is carried out above ambient temperature. In an embodiment of the invention, step 1 is carried out at 60° C. in tetrahydrofuran. In an embodiment of the invention, step 1 is carried out at 60° C. in tetrahydrofuran and is stirred for at least 1 hr.

In an embodiment of the invention, $M^1$ and $M^2$ are the same metal.

In an embodiment of the invention, $M^1$ and $M^2$ are different metals.

In an embodiment of the invention, $C_6F_6$ is combined with ca. 2 molar equivalents of $[Na][C_5H_5]$ in the presence of an ethereal solvent. In an embodiment of the invention, $C_6F_6$ is added to ca. 2 molar equivalents of $[Na][C_5H_5]$ in the presence of an ethereal solvent. In an embodiment of the invention, $C_6F_6$ is added to ca. 2 molar equivalents of $[Na][C_5H_5]$ in the presence of THF. In an embodiment of the invention, $C_6F_6$ is added to ca. 2 molar equivalents of $[Na][C_5H_5]$ in the presence of an ethereal solvent over at least 30 min. In another embodiment of the invention, $C_6F_6$ is added to ca. 2 molar equivalents of $[Na][C_5H_5]$ in the presence of THF over at least 60 min. In an embodiment of the invention, $C_6F_6$ is added to ca. 2 molar equivalents of $[Na][C_5H_5]$ in the presence of THF over at least 30 min to give a first reaction mixture which is stirred at 60° C. for at least 1 hr.

In an embodiment of the invention, $C_6F_6$ is combined with an approximately equimolar amount of a 1:1 mixture of $[Na][C_5H_5]$ and NaH in the presence of an ethereal solvent. In an embodiment of the invention, $C_6F_6$ is added to an approximately equimolar amount of a 1:1 mixture of $[Na][C_5H_5]$ and NaH in the presence of ethereal solvent. In an embodiment of the invention, $C_6F_6$ is added to an approximately equimolar amount of a 1:1 mixture of $[Na][C_5H_5]$ and NaH in the presence of THF. In an embodiment of the invention, $C_6F_6$ is added to an approximately equimolar amount of a 1:1 mixture of $[Na][C_5H_5]$ and NaH in the presence of an ethereal solvent over at least 30 min. In an embodiment of the invention, $C_6F_6$ is added to an approximately equimolar amount of a 1:1 mixture of [Na][C$_5$H$_5$] and NaH in the presence of THF over at least 60 min. In an embodiment of the invention, C$_6$F$_6$ is added to an approximately equimolar amount of a 1:1 mixture of [Na][C$_5$H$_5$] and NaH in the presence of THF over at least 30 min to give a first reaction mixture which is stirred at ≥40° C. for at least 3 hrs.

In the present invention, the compound [M$^1$/M$^2$][(C$_6$F$_5$)C$_5$H$_4$] having the structure II is not isolated from the first reaction mixture before carrying out step 2 which is described below.

Step 2. In the second step, chlorotrimethylsilane (ClSiMe$_3$) is combined with the first reaction mixture obtained in step 1 and which comprises the compound [M$^1$/M$^2$][(C$_6$F$_5$)C$_5$H$_4$] to give a second reaction mixture comprising 1,3-(SiMe$_3$)(C$_6$F$_5$)C$_5$H$_4$ having the structure (III).

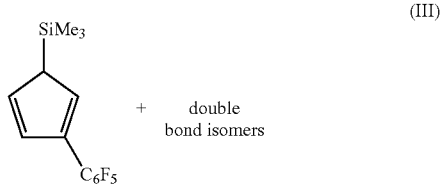

+ double bond isomers                               (III)

Without wishing to be bound by theory, the compound 1,3-(SiMe$_3$)(C$_6$F$_5$)C$_5$H$_4$ having the structure (III) may exist as a mixture of so called "double bond isomers" which are present in various amounts. By the term "double bond isomer" it is meant that the position of the sp$^3$ hybridized carbon present in the 5 member cyclopentadiene ring structure may vary with respect to the —SiMe$_3$ and —C$_6$F$_5$ groups.

The ClSiMe$_3$ is preferably combined or added in neat form, but may also be combined or added in an appropriate solvent such as an ethereal solvent. For example, THF can be used as a transfer solvent if desired. Although the current invention contemplates any order of addition, in order to avoid using a new reaction vessel in an embodiment of the invention, the ClSiMe$_3$ must be added to the first reaction mixture and not in the reverse order.

In the present invention, it is essential to use at least about 2 molar equivalents of ClSiMe$_3$ for combination with the first reaction mixture. Without wishing to be bound by theory, addition of 2 molar equivalents of ClSiMe$_3$, provides 1 molar equivalent of ClSiMe$_3$ to react with the (C$_6$F$_5$)C$_5$H$_4^-$ anion, and 1 molar equivalent of ClSiMe$_3$ to react with metal fluorides such as sodium fluoride NaF also present in the first reaction mixture. Reaction of ClSiMe$_3$ with NaF (or KF or LiF) gives FSiMe$_3$ and NaCl (or KCl or LiCl). We have found that removal of NaF (or KF or LiF) from the first reaction mixture helps to achieve reasonable overall yield of the ligand precursor, since NaF (or KF or LiF) reacts with silylated cyclopentadienyl compounds (e.g. 1,3-(SiMe$_3$)(C$_6$F$_5$)C$_5$H$_4$ in the second reaction mixture or 1,3,4-(SiMe$_3$)(C$_6$F$_5$)(R)C$_5$H$_3$ in the fourth reaction mixture, see below) to give unwanted side products, such as those obtained by fluorodesilylation.

As shown in the examples section, the use of 2 molar equivalents of ClSiMe$_3$ provides for higher overall yield of the desired 1,3,4-(SiMe$_3$)(C$_6$F$_5$)(R)C$_5$H$_3$ product when fluoride salts are not removed by time consuming filtration steps. For example, use of a single molar equivalent of ClSiMe$_3$ gave rise to almost no desired 1,3,4-(SiMe$_3$)(C$_6$F$_5$)(R)C$_5$H$_3$ product (see Comparative Example 2) due to decomposition by fluoride driven desilylation.

The data shown in Table 1 demonstrate that the order of addition and the speed of addition of ClSiMe$_3$ can affect the yield of the desired monosilylated species 1,3-(SiMe$_3$)(C$_6$F$_5$)C$_5$H$_4$.

TABLE 1

| Mono/Di-Silylated Product Yields | | | |
|---|---|---|---|
| Order of Addition | ClSiMe$_3$ is added to the first reaction mixture | ClSiMe$_3$ is added to the first reaction mixture | The first reaction mixture is added to ClSiMe$_3$ |
| Molar Equivalents of ClSiMe$_3$ | 2 | 2 | 2 |
| Form of ClSiMe$_3$ | Neat | Neat | 25 vol % solution in THF |
| Time of ClSiMe$_3$ addition | 1 min (rapid) | 15 min (slow) | 1 min (rapid) |
| Yield[1] of 1,3-(SiMe$_3$)(C$_6$F$_5$)C$_5$H$_4$ | 65.0 | 48.9 | 71.8 |
| Yield[1] of (SiMe$_3$)$_2$(C$_6$F$_5$)C$_5$H$_3$ | 6.5 | 24.1 | 1.9 |

Note
[1] the yield of mono and disilylated products was determined by subjecting the mixture obtained (after combination with ClSiMe$_3$) to gas chromatography coupled with mass spectrum detection (GC-MS).

Table 1 shows that addition of the first reaction mixture to ClSiMe$_3$ generates minimal amounts (<2%) of undesired disilylated product (SiMe$_3$)$_2$(C$_6$F$_5$)C$_5$H$_3$, while addition of ClSiMe$_3$ to the first reaction mixture generates significant levels of disilylated product. This is perhaps not unexpected, since addition of ClSiMe$_3$ to the first reaction mixture keeps the basic anion (C$_6$F$_5$)C$_5$H$_4^-$ in excess, so that deprotonation of the desired monosilylated product may lead to further reaction with ClSiMe$_3$ to give (SiMe$_3$)$_2$(C$_6$F$_5$)C$_5$H$_3$. This is especially true when ClSiMe$_3$ is slowly added to a mixture comprising the anion (C$_6$F$_5$)C$_5$H$_4^-$ (where the yield of (SiMe$_3$)$_2$(C$_6$F$_5$)C$_5$H$_3$ is ca. 24%).

In order to suppress the formation of (SiMe$_3$)$_2$(C$_6$F$_5$)C$_5$H$_3$ as much as possible while circumventing the need for a new reaction vessel, it is therefore preferable to rapidly add the ClSiMe$_3$ to the first reaction mixture and to do so at reduced temperatures. Alternatively, when using a new reaction vessel it is preferable to add the first reaction mixture comprising [M$^1$/M$^2$][(C$_6$F$_5$)C$_5$H$_4$] directly to ClSiMe$_3$ in order to keep ClSiMe$_3$ in excess, thereby suppressing as much as possible, the formation of (SiMe$_3$)$_2$(C$_6$F$_5$)C$_5$H$_3$.

In an embodiment of the invention, ClSiMe$_3$ is added rapidly to the first reaction mixture all at once as a batch addition. In an embodiment of the invention, ClSiMe$_3$ is added rapidly to the first reaction mixture all at once as a batch addition at temperatures below ambient temperature. In an embodiment of the invention, 2 molar equivalents of ClSiMe$_3$ are added rapidly to the first reaction mixture all at once as a batch addition at temperatures below ambient temperature.

In an embodiment of the invention, the first reaction mixture comprising [M$^1$/M$^2$][(C$_6$F$_5$)C$_5$H$_4$] is added rapidly to ClSiMe$_3$. In an embodiment of the invention, the first reaction mixture comprising [M$^1$/M$^2$][(C$_6$F$_5$)C$_5$H$_4$] is added slowly to ClSiMe$_3$. In an embodiment of the invention, the first reaction mixture comprising [M$^1$/M$^2$][(C$_6$F$_5$)C$_5$H$_4$] is added to ClSiMe$_3$ at temperatures below ambient temperature. In an embodiment of the invention, the first reaction mixture comprising [M$^1$/M$^2$][(C$_6$F$_5$)C$_5$H$_4$] is added to 2 molar equivalents of ClSiMe$_3$.

In an embodiment of the invention, at least 2 molar equivalents of ClSiMe$_3$ are added to the first reaction mixture over less than 5 min. In an embodiment of the invention, at least 2 molar equivalents of ClSiMe$_3$ are added to the first reaction mixture over less than 5 min at temperatures below ambient temperature. In an embodiment of the invention, 2 molar equivalents of ClSiMe$_3$ are added to the first reaction mixture over less than 5 min. In an embodiment of the invention, 2 molar equivalents of ClSiMe$_3$ are added to the first reaction mixture over less than 5 min at temperatures below ambient temperature. In an embodiment of the invention, at least 2 molar equivalents of ClSiMe$_3$ are added to the first reaction mixture over less than 5 min at 0° C. or less. In an embodiment of the invention, 2 molar equivalents of ClSiMe$_3$ are added to the first reaction mixture over less than 5 min at 0° C. or less.

In an embodiment of the invention, the first reaction mixture comprising [M$^1$/M$^2$][(C$_6$F$_5$)C$_5$H$_4$] is added to at least 2 molar equivalents of ClSiMe$_3$. In an embodiment of the invention, the first reaction mixture comprising [M$^1$/M$^2$][(C$_6$F$_5$)C$_5$H$_4$] is added slowly to at least 2 molar equivalents of ClSiMe$_3$. In an embodiment of the invention, the first reaction mixture comprising [M$^1$/M$^2$][(C$_6$F$_5$)C$_5$H$_4$] is added quickly to at least 2 molar equivalents of ClSiMe$_3$. In an embodiment of the invention, the first reaction mixture comprising [M$^1$/M$^2$][(C$_6$F$_5$)C$_5$H$_4$] is added slowly to 2 molar equivalents of ClSiMe$_3$. In an embodiment of the invention, the first reaction mixture comprising [M$^1$/M$^2$][(C$_6$F$_5$)C$_5$H$_4$] is added quickly to 2 molar equivalents of ClSiMe$_3$.

In an embodiment of the invention, a rigorously dried ethereal solvent is used as a solvent during any or all of steps 1-4. Without wishing to be bound by theory, use of a rigorously dried solvent helps to avoid the formation of undesirable side products, such as those generated by protodesilylation reactions; e.g. products obtained from hydrolysis of the SiMe$_3$ group from the cyclopentadienyl moiety in 1,3-(SiMe$_3$)(C-$_6$F$_5$)C$_5$H$_4$. Any suitable solvent drying methods known to those skilled in the art may be employed to dry the ethereal solvent, such as for example use of drying agents (e.g. molecular sieves, alumina etc.), optionally in combination with distillation techniques.

In embodiments of the invention, an ethereal solvent having less than 50 ppm or less than 25 ppm, or less than 20 ppm of water is used as a solvent during any or all of steps 1-4.

In embodiments of the invention, a tetrahydrofuran (THF) solvent having less than 50 ppm or less than 25 ppm, or less than 20 ppm of water is used as a solvent during any or all of steps 1-4.

In the present invention, the second reaction mixture is used directly in step 3, without isolating 1,3-(SiMe$_3$)(C$_6$F$_5$)C$_5$H$_4$.

Step 3. In the third step, a second base M$^3$B$^2$ is combined with the second reaction mixture obtained in step 2 and which comprises the compound 1,3-(SiMe$_3$)(C-$_6$F$_5$)C$_5$H$_4$ to give a third reaction mixture comprising [M$^1$/M$^2$/M$^3$][1,3-(SiMe$_3$)(C$_6$F$_5$)C$_5$H$_3$] which has the structure IV,

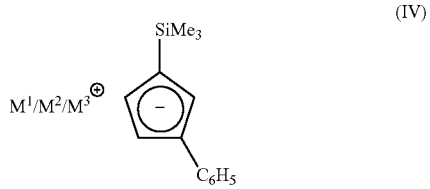

(IV)

where M$^1$/M$^2$/M$^3$ indicates that mixed metal salts of the anion 1,3-(SiMe$_3$)(C$_6$F$_5$)C$_5$H$_3$$^-$ may be present when M$^1$≠M$^2$≠M$^3$, although M$^1$ may also be the same or different metal as M$^2$ and/or M$^3$ (e.g. M$^1$=M$^2$=M$^3$, or M$^1$=M$^2$≠M$^3$, or M$^1$=M$^3$≠M$^2$, or M$^1$≠M$^2$=M$^3$)

Although any order of addition is contemplated by the present invention, in order to avoid using a new reaction vessel in an embodiment of the invention, M$^3$B$^2$ must be added to the second reaction mixture comprising 1,3-(SiMe$_3$)(C$_6$F$_5$)C$_5$H$_4$ and not in the reverse order. The base M$^3$B$^2$ may be added or combined as a solution in an ethereal solvent, or as a solution or suspension in a hydrocarbon solvent.

The base M$^3$B$^2$ is preferably a base selected from the group consisting of metal hydride, metal alkylide (including cyclic alkylides, or aromatic cyclic alkylides such as those based on the cyclopentadienide anion), metal amide and metal alkoxide bases, were M$^3$ is preferably selected from the group consisting of Li$^+$, Na$^+$, and K$^+$.

In an embodiment of the invention, the base M$^3$B$^2$ is an alkyl lithium compound. In an embodiment of the invention, the base M$^3$B$^2$ is a sodium alkylide compound.

In embodiments of the invention, the base M$^3$B$^2$ is a sodium alkoxide compound or a potassium alkoxide compound.

Without wishing to be bound by theory, the use of a less nucleophilic base such as an alkoxide anion (relative to for example an alkylide base) in step 3 mitigates the formation of unwanted species by nucleophilic displacement of an aromatic fluorine atom from the perfluorophenyl group C$_6$F$_5$ present in 1,3-(SiMe$_3$)(C$_6$F$_5$)C$_5$H$_4$. This may be especially true in a polar ethereal solvent which facilitates nucleophilic aromatic substitution reactions. Also, use of a less aggressive nucleophilic base such as an alkoxide anion (relative to for example an alkylide base) provides a less exothermic reaction with less heat formation which may be desirable at larger scales, especially commercially relevant scales (e.g. ≥500 mmol).

In an embodiment of the invention, the base M$^3$B$^2$ is n-butyl lithium (n-BuLi). In an embodiment of the invention, the base M$^3$B$^2$ is sodium cyclopentadienide ([Na][C$_5$H$_5$]). In embodiments of the invention, the base M$^3$B$^2$ is sodium tert-butoxide (NaOtBu) or potassium tert-butoxide (KOtBu).

In an embodiment of the invention, ca. 1 molar equivalent of base M$^3$B$^3$ is combined with the second reaction mixture comprising 1,3-(SiMe$_3$)(C$_6$F$_5$)C$_5$H$_4$.

In an embodiment of the invention, ca. 1 molar equivalent of base M$^3$B$^3$ is added to the second reaction mixture comprising 1,3-(SiMe$_3$)(C$_6$F$_5$)C$_5$H$_4$.

In an embodiment of the invention, sodium tert-butoxide (NaOtBu) is added as a solution in an ethereal solvent to the second reaction mixture comprising 1,3-(SiMe$_3$)(C$_6$F$_5$)C$_5$H$_4$. In an embodiment of the invention, sodium tert-butoxide (NaOtBu) is added as a solution in THF to the second reaction mixture comprising 1,3-(SiMe$_3$)(C-$_6$F$_5$)C$_5$H$_4$. In an embodiment of the invention, sodium tert-butoxide (NaOtBu) is added as a solution in THF to the second reaction mixture comprising 1,3-(SiMe$_3$)(C$_6$F$_5$)C$_5$H$_4$ at a temperature below ambient temperature. In an embodiment of the invention, sodium tert-butoxide (NaOtBu) is added as a solution in THF to the second reaction mixture comprising 1,3-(SiMe$_3$)(C$_6$F$_5$)C$_5$H$_4$ at 0° C. or less. In an embodiment of the invention, a molar equivalent of sodium tert-butoxide (NaOtBu) is added as a solution in THF to the second reaction mixture comprising 1,3-(SiMe$_3$)(C$_6$F$_5$)C$_5$H$_4$ at 0° C. or less.

In an embodiment of the invention, an alkyl lithium compound is added as a solution in an ethereal solvent or a hydrocarbon solvent to the second reaction mixture comprising 1,3-(SiMe$_3$)(C$_6$F$_5$)C$_5$H$_4$. In an embodiment of the invention, an alkyl lithium compound is added as a solution in an ethereal solvent or a hydrocarbon solvent to the second reaction mixture comprising 1,3-$(SiMe_3)(C_6F_5)C_5H_4$ at a temperature of 0° C. or less. In an embodiment of the invention, a molar equivalent of n-butyllithium is added as a solution in an ethereal solvent or a hydrocarbon solvent to the second reaction mixture comprising 1,3-$(SiMe_3)(C_6F_5)C_5H_4$ at temperature of 0° C. or less.

In an embodiment of the invention, $[Na][C_5H_5]$ is added as a solution in an ethereal solvent to the second reaction mixture comprising 1,3-$(SiMe_3)(C_6F_5)C_5H_4$. In an embodiment of the invention, $[Na][C_5H_5]$ is added as a solution in an ethereal solvent to the second reaction mixture comprising 1,3-$(SiMe_3)(C_6F_5)C_5H_4$ at a temperature of 0° C. or less. In an embodiment of the invention, an equivalent of $[Na][C_5H_5]$ is added as a solution in an ethereal solvent to the second reaction mixture comprising 1,3-$(SiMe_3)(C_6F_5)C_5H_4$ at temperature of 0° C. or less.

In the present invention, the third reaction mixture is used directly in step 4, without isolating $[M^1/M^2/M^3][(SiMe_3)(C_6F_5)C_5H_3]$.

Step 4. In the fourth step, a compound RX, is combined with the third reaction mixture obtained in step 3 which comprises the compound $[M^1/M^2/M^3][1,3\text{-}(SiMe_3)(C_6F_5)C_5H_3]$ to give a fourth reaction mixture comprising the ligand precursor compound 1,3,4-$(SiMe_3)(C_6F_5)(R)C_5H_3$ which has the structure (V) where R is a primary or a secondary alkyl group which is further defined below.

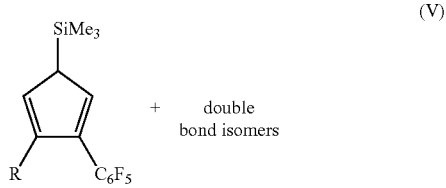

(V) + double bond isomers

Without wishing to be bound by theory, the compound 1,3,4-$(SiMe_3)(C_6F_5)(R)C_5H_3$ having the structure (V) may exists as a mixture of so called "double bond isomers" which are present in various amounts. By the term "double bond isomer" it is meant that the position of the $sp^3$ hybridized carbon present in the 5 member cyclopentadiene ring structure may vary with respect to the —$SiMe_3$, —$C_6F_5$ and —R groups).

Although the current invention contemplates any order of addition, in order to avoid using a new reaction vessel in an embodiment of the invention, RX must be added to the third reaction mixture comprising $[M^1/M^2/M^3][1,3\text{-}(SiMe_3)(C_6F_5)C_5H_3]$ and not in the reverse order.

In the present invention, the RX compound serves as a source of R which is a primary or secondary alkyl group. A primary alkyl group includes alkyl groups and alkylaryl groups. A primary alkyl group may be branched or unbranched and may include unsaturated or aromatic moieties, so long as the alpha carbon (e.g. immediately attached to X) is a primary carbon (i.e. is bonded to one carbon atom). A secondary alkyl group includes alkyl groups and alkylaryl groups. A secondary alkyl group may be branched or unbranched and may include unsaturated or aromatic moieties, so long as the alpha carbon (e.g. immediately attached to X) is a secondary carbon (i.e. is bonded to two carbon atoms). The X is a leaving group, preferably a leaving group which is readily displaceable by a nucleophile such as a cyclopentadienide anion or a singly or multiply substituted cyclopentadienide anion. Suitable leaving groups include halides such as for example Cl, Br and I, and sulfonates (—$SO_3R^2$) such as for example a mesylate (where $R^2$ is methyl), a tosylate (where $R^2$ is —$C_6H_4CH_3$) or a triflate (where $R^2$ is —$CF_3$).

In an embodiment of the invention, the R group is a primary or secondary alkyl group which may be substituted by one or more heteroatom or heteroatom containing group. Hence, the primary or secondary alkyl group may be substituted with one or more halogen heteroatom such as a fluorine, chlorine, bromine, or iodine. The primary or secondary alkyl group may also be substituted with an oxygen atom forming an alkyloxy or an aryloxy group. Other possible heteroatoms which may be present in the primary or secondary alkyl group R include B, Al, Ga, In, Si, Ge, Sn, N, P, As, O, S, or Se. Examples of heteroatom containing groups are groups containing one or more atoms selected from B, Al, Ga, In, Si, Ge, Sn, N, P, As, O, S, or Se, or groups containing one or more halogen atoms.

In an embodiment of the invention, the R group is a primary alkyl group which is unsubstituted by a heteroatom or a heteroatom containing group.

In an embodiment of the invention, the R group is a primary alkyl group which is substituted by one or more heteroatom and/or a heteroatom containing group.

In an embodiment of the invention, the R group is a primary alkyl group which is substituted by one or more heteroatom or a heteroatom containing group.

In an embodiment of the invention, the R group is a primary alkyl group which is substituted by one or more heteroatom.

In an embodiment of the invention, the R group is a primary alkyl group which is substituted by one or more halide atom.

In an embodiment of the invention, the alkyl group R is a primary alkyl group or a primary alkylaryl group. In an embodiment of the invention, R is a primary alkyl group having 1 to 20 carbon atoms and which may optionally be substituted with at least one halide atom. In an embodiment of the invention, R is a straight chain alkyl group having 1 to 20 carbon atoms and which may optionally be substituted with at least one halide atom. In an embodiment of the invention, the R group is a —$CH_2R'$ group where R' is a straight chain or branched alkyl group, an aryl group, an arylalkyl group, or an alkylaryl group all of which may be optionally substituted with at least one halide atom. In an embodiment of the invention, R is a straight chain alkyl group having 1 to 12 carbon atoms and which may optionally be substituted with at least one halide atom. In an embodiment of the invention, the R group is a —$CH_2R'$ group where R' is a straight chain or branched alkyl group, an aryl group, an arylalkyl group, or an alkylaryl group all of which may be optionally substituted with at least one fluoride atom.

In an embodiment of the invention, R is a primary alkyl group selected from the group consisting of methyl, ethyl, n-propyl, n-butyl, n-pentyl, n-hexyl, n-heptyl, n-octyl, n-nonyl, n-decyl, n-dodecyl and benzyl.

In an embodiment of the invention, the compound RX is an alkyl halide selected so that R is a primary alkyl group or a primary alkylaryl group. In an embodiment of the invention, the compound RX is an alkyl halide selected so that R is a primary alkyl group having 1 to 20 carbon atoms and which may optionally be substituted with at least one halide atom. In an embodiment of the invention, the compound RX is an alkyl halide selected so that R is a straight chain alkyl group having 1 to 20 carbon atoms and which may optionally be substituted with at least one halide atom. In an embodiment of the invention, the compound RX is an alkyl halide selected so that the R group is a —$CH_2R'$ group where R' is a straight chain or branched alkyl group, an aryl group, an arylalkyl group, or an alkylaryl group all of which may be optionally substituted with at least one halide atom. In an embodiment of the invention, the compound RX is an alkyl halide selected so that R is a straight chain alkyl group having 1 to 12 carbon atoms and which may optionally be substituted with at least one halide atom. In an embodiment of the invention, the compound RX is an alkyl halide selected so that the R group is a —CH$_2$R' group where R' is a straight chain or branched alkyl group, an aryl group, an arylalkyl group, or an alkylaryl group all of which may be optionally substituted with at least one fluoride atom.

In embodiments of the invention, X is a halide selected from chloride, bromide, and iodide.

In embodiments of the invention, RX is selected from the group consisting of methyl halide, ethyl halide, n-propyl halide, n-butyl halide, n-pentyl halide, n-hexyl halide, n-heptyl halide, n-octyl halide, benzyl halide and perfluorophenyl benzyl halide where halide is chloride, bromide or iodide.

In embodiments of the invention, RX is selected from the group consisting of methyl bromide, ethyl bromide, n-propyl bromide, n-butyl bromide, n-pentyl bromide, n-hexyl bromide, n-heptyl bromide, n-octyl bromide and benzyl bromide.

In embodiments of the invention, RX is selected from the group consisting of n-propyl bromide, n-butyl bromide, n-pentyl bromide, n-hexyl bromide, n-heptyl bromide, and n-octyl bromide.

In an embodiment of the invention, RX is n-propyl bromide.

In an embodiment of the invention, RX is benzyl bromide.

In an embodiment of the invention, RX is a fluorinated benzyl bromide having the formula C$_6$F$_5$CH$_2$Br.

In an embodiment of the invention, RX is combined with the third reaction mixture comprising [M$^1$/M$^2$/M$^3$][1,3-(SiMe$_3$)(C$_6$F$_5$)C$_5$H$_3$] in a molar ratio of greater than 1:1. In another embodiment of the invention, RX is combined with the third reaction mixture comprising [M$^1$/M$^2$/M$^3$][1,3-(SiMe$_3$)(C$_6$F$_5$)C$_5$H$_3$] in a molar ratio of about 1.5:1. In another embodiment of the invention, RX is combined with the third reaction mixture comprising [M$^1$/M$^2$/M$^3$][1,3-(SiMe$_3$)(C$_6$F$_5$)C$_5$H$_3$] in a molar ratio of about 1.25:1. In a further embodiment of the invention, RX is combined with the third reaction mixture comprising [M$^1$/M$^2$/M$^3$][1,3-(SiMe$_3$)(C$_6$F$_5$)C$_5$H$_3$] in a molar ratio of about 1:1.

In an embodiment of the invention, RX is added to the third reaction mixture comprising [M$^1$/M$^2$/M$^3$][1,3-(SiMe$_3$)(C$_6$F$_5$)C$_5$H$_3$] in a molar ratio of greater than 1:1. In another embodiment of the invention, RX is added to the third reaction mixture comprising [M$^1$/M$^2$/M$^3$][1,3-(SiMe$_3$)(C$_6$F$_5$)C$_5$H$_3$] in a molar ratio of about 1.5:1. In another embodiment of the invention, RX is added to the third reaction mixture comprising [M$^1$/M$^2$/M$^3$][1,3-(SiMe$_3$)(C$_6$F$_5$)C$_5$H$_3$] in a molar ratio of about 1.25:1. In a further embodiment of the invention, RX is added to the third reaction mixture comprising [M$^1$/M$^2$/M$^3$][1,3-(SiMe$_3$)(C$_6$F$_5$)C$_5$H$_3$] in a molar ratio of about 1:1.

In an embodiment of the invention, RX is added to the third reaction mixture comprising [M$^1$/M$^2$/M$^3$][1,3-(SiMe$_3$)(C$_6$F$_5$)C$_5$H$_3$] slowly over at least a 15 min period at below ambient temperature. In another embodiment of the invention, RX is added to the third reaction mixture comprising [M$^1$/M$^2$/M$^3$][1,3-(SiMe$_3$)(C$_6$F$_5$)C$_5$H$_3$] slowly over at least a 30 min period at below ambient temperature. In a further embodiment of the invention, RX is added to the third reaction mixture [M$^1$/M$^2$/M$^3$][1,3-(SiMe$_3$)(C$_6$F$_5$)C$_5$H$_3$] slowly over at least a 60 min period at below ambient temperature.

In an embodiment of the invention, RX is added to the third reaction mixture comprising [M$^1$/M$^2$/M$^3$][1,3-(SiMe$_3$)(C$_6$F$_5$)C$_5$H$_3$] rapidly in less than about a 5 min period.

In an embodiment of the invention, RX is added rapidly to the third reaction mixture all at once as a batch addition. In an embodiment of the invention, RX is added rapidly to the third reaction mixture all at once as a batch addition at temperatures below ambient temperature. In an embodiment of the invention, less than 1 molar equivalent of RX is added rapidly to the third reaction mixture all at once as a batch addition at temperatures below ambient temperature. In an embodiment of the invention, ca. 1 molar equivalent of RX is added rapidly to the third reaction mixture all at once as a batch addition at temperatures below ambient temperature. In an embodiment of the invention, ca. 1.5 molar equivalents of RX are added rapidly to the third reaction mixture all at once as a batch addition at temperatures below ambient temperature. In an embodiment of the invention, a molar excess of RX is added rapidly to the third reaction mixture all at once as a batch addition at temperatures below ambient temperature.

The compound RX may be added neat or as a solution in an appropriate solvent such as an ethereal solvent or a hydrocarbon solvent.

In embodiments of the invention, RX is combined with the third reaction mixture comprising [M$^1$/M$^2$/M$^3$][1,3-(SiMe$_3$)(C$_6$F$_5$)C$_5$H$_3$] at or below ambient temperature. In an embodiment of the invention, RX is combined with the third reaction mixture comprising [M$^1$/M$^2$/M$^3$][1,3-(SiMe$_3$)(C$_6$F$_5$)C$_5$H$_3$] at around 0° C.

In embodiments of the invention, RX is added to the third reaction mixture comprising [M$^1$/M$^2$/M$^3$][1,3-(SiMe$_3$)(C$_6$F$_5$)C$_5$H$_3$] at or below ambient temperature. In an embodiment of the invention, RX is added to the third reaction mixture comprising [M$^1$/M$^2$/M$^3$][1,3-(SiMe$_3$)(C$_6$F$_5$)C$_5$H$_3$] at around 0° C.

Although the use of an alkyl halide is preferred for delivery of a primary or secondary alkyl group to the 1,3-(SiMe$_3$)(C$_6$F$_5$)C$_5$H$_3^-$ anion is step 4, the present invention further contemplates the use of RX compounds, where R is defined as above, and X is a non-halide leaving group which can be displaced by a nucleophile such as 1,3-(SiMe$_3$)(C$_6$F$_5$)C$_5$H$_3^-$. Such leaving groups may be for example a sulfonate group such as a tosylate group, a mesylate group or a triflate group, but other leaving groups known in the art may also be used so long as they can be displaced by the 1,3-(SiMe$_3$)(C$_6$F$_5$)C$_5$H$_3^-$ anion.

Scale

The present invention is useful for the preparation of the ligand precursor 1,3,4-(SiMe$_3$)(C$_6$F$_5$)(R)C$_5$H$_3$ at any scale, but is particularly useful at larger scale. By "larger scale", it is meant that the method of the present invention can be used to prepare 1,3,4-(SiMe$_3$)(C$_6$F$_5$)(R)C$_5$H$_3$ at a scale of 500 mmol (based on the amount in millimoles of the starting reagent C$_6$F$_6$) or more.

Work-Up

The method for making the ligand precursor compound 1,3,4-(SiMe$_3$)(C-$_6$F$_5$)(R)C$_5$H$_3$ as described above can further comprise isolating or improving the purity of 1,3,4-(SiMe$_3$)(C$_6$F$_5$)(R)C$_5$H$_3$.

For example, the method of the invention can further comprise steps such as removing volatile components from the fourth reaction mixture under vacuum, filtration of the fourth reaction mixture, distillation of the fourth reaction mixture and aqueous work-up of the fourth reaction mixture.

In an embodiment of the invention, the fourth reaction mixture has its volatiles removed under vacuum to give a first residue comprising 1,3,4-(SiMe$_3$)(C$_6$F$_5$)(R)C$_5$H$_3$, followed by extraction of the first residue with a hydrocarbon solvent (e.g. pentane, heptane, etc.) to give a hydrocarbon solution comprising 1,3,4-$(SiMe_3)(C_6F_5)(R)C_5H_3$, followed by filtration of the hydrocarbon solution to remove inorganic salts and to give a filtrate comprising 1,3,4-$(SiMe_3)(C_6F_5)(R)C_5H_3$, followed by removal of volatiles from the filtrate under vacuum to give a second residue comprising 1,3,4-$(SiMe_3)(C_6F_5)(R)C_5H_3$.

In an embodiment of the invention, the fourth reaction mixture comprising the ligand precursor compound 1,3,4-$(SiMe_3)(C_6F_5)(R)C_5H_3$ is subjected to an aqueous work-up in order to reduce the amount of inorganic salts present. An aqueous work-up is an attractive alternative to a filtration, due to the simplicity of performing a liquid-liquid extraction. This is especially true for large scale synthetic preparations where filtration steps (to remove for example finely divided inorganic salts) can be very time consuming. An aqueous work-up also allows for the removal of other potentially problematic water soluble compounds that may be present depending on the reagents used. For example, use of a sodium alkoxide as a base in step 3 generates an alcohol byproduct. The alcohol byproduct can be removed by aqueous work-up.

Prior to carrying out the aqueous liquid extraction, the ethereal solvent (e.g. THF) present in the fourth reaction mixture may optionally be removed under vacuum. However, for convenience, simple dilution of the fourth reaction mixture comprising 1,3,4-$(SiMe_3)(C_6F_5)(R)C_5H_3$ with a hydrocarbon solvent (e.g. pentane, heptane, etc.) followed by extraction of salts with an aqueous solution may be preferable in some embodiments of the invention. Also for convenience, in some embodiments of the invention where the ethereal solvent used is sufficiently immiscible with an aqueous solution, the fourth reaction mixture may be directly extracted with an aqueous solution.

In an embodiment of the invention, the fourth reaction mixture is diluted by a hydrocarbon solvent prior to an aqueous workup. In an embodiment of the invention, the fourth reaction mixture is diluted by at least three times its volume with a hydrocarbon solvent prior to an aqueous workup. In an embodiment of the invention, when the fourth reaction mixture is prepared in the presence of THF as the ethereal solvent, it is diluted by at least three times its volume with a hydrocarbon solvent prior to an aqueous workup. In an embodiment of the invention, the fourth reaction mixture is concentrated by removing volatiles under vacuum, followed by dilution by at least three times its volume with a hydrocarbon solvent, prior to an aqueous workup.

In the present invention, it is preferable to use a weakly acidic aqueous solution for a liquid-liquid extraction step. Without wishing to be bound by theory, use of a weakly acidic solution mitigates the decomposition of 1,3,4-$(SiMe_3)(C_6F_5)(R)C_5H_3$ by loss of a trimethylsilyl group through carbon-silicon bond cleavage, since neutral or basic conditions are thought to facilitate such a reaction.

A weakly acidic aqueous solution can be prepared by mixing any suitable acid or weak acid with water in concentrations which provide a pH level of slightly below 7. For example, a pH of from about 3 to just below 7.0 may be used. By way of non-limiting example only, a mildly acidic aqueous solution can be prepared by dissolving $NH_4Cl$ in water to provide a $NH_4Cl$ solution or a $NH_4Cl$ saturated solution.

The liquid-liquid extraction to remove inorganic salts may involve a number of extraction, agitation and separation steps. Separation of a hydrocarbon solution containing 1,3,4-$(SiMe_3)(C_6F_5)(R)C_5H_3$ from an aqueous layer, followed by removal of volatiles under vacuum gives a residue comprising 1,3,4-$(SiMe_3)(C_6F_5)(R)C_5H_3$ with reduced amounts of inorganic salt (e.g. LiBr, NaBr) present.

In an embodiment of the invention, the fourth reaction mixture comprising the ligand precursor compound 1,3,4-$(SiMe_3)(C_6F_5)(R)C_5H_3$ is subjected to the following steps:
 i) volatiles are removed under vacuum to give a first residue comprising 1,3,4-$(SiMe_3)(C_6F_5)(R)C_5H_3$;
 ii) the residue is combined with a hydrocarbon solvent to give a hydrocarbon solution comprising 1,3,4-$(SiMe_3)(C_6F_5)(R)C_5H_3$;
 iii) the hydrocarbon solution is subjected to extraction with a weakly acidic aqueous solution and the hydrocarbon solution is retained after phase separation;
 iv) volatiles are removed from the hydrocarbon solution under vacuum to give a second residue comprising 1,3,4-$(SiMe_3)(C_6F_5)(R)C_5H_3$.

In an embodiment of the invention, the fourth reaction mixture comprising the ligand precursor compound 1,3,4-$(SiMe_3)(C_6F_5)(R)C_5H_3$ is subjected to the following steps:
 i) volatiles are removed under vacuum to give a first residue comprising 1,3,4-$(SiMe_3)(C_6F_5)(R)C_5H_3$;
 ii) the residue is combined with a hydrocarbon solvent to give a hydrocarbon solution comprising 1,3,4-$(SiMe_3)(C_6F_5)(R)C_5H_3$;
 iii) the hydrocarbon solution is subjected to extraction with a weakly acidic aqueous solution to at least partially remove inorganic salts from the hydrocarbon solution comprising 1,3,4-$(SiMe_3)(C_6F_5)(R)C_5H_3$;
 iv) volatiles are removed from the hydrocarbon solution under vacuum to give a product residue comprising 1,3,4-$(SiMe_3)(C_6F_5)(R)C_5H_3$ as the majority species by weight.

In an embodiment of the invention, the fourth reaction mixture comprising the ligand precursor compound 1,3,4-$(SiMe_3)(C_6F_5)(R)C_5H_3$ is subjected to the following steps:
 i) the fourth reaction mixture is diluted by addition of a hydrocarbon solvent to give a hydrocarbon solution comprising 1,3,4-$(SiMe_3)(C_6F_5)(R)C_5H_3$;
 ii) the hydrocarbon solution is subjected to extraction with a weakly acidic aqueous solution and the hydrocarbon solution is retained after phase separation;
 iii) volatiles are removed from the hydrocarbon solution under vacuum to give a residue comprising 1,3,4-$(SiMe_3)(C_6F_5)(R)C_5H_3$.

In an embodiment of the invention, the fourth reaction mixture comprising the ligand precursor compound 1,3,4-$(SiMe_3)(C_6F_5)(R)C_5H_3$ is subjected to the following steps:
 i) the fourth reaction mixture is diluted by addition of a hydrocarbon solvent to give a product mixture comprising 1,3,4-$(SiMe_3)(C_6F_5)(R)C_5H_3$;
 ii) the product mixture is subjected to extraction with a weakly acidic aqueous solution to at least partially remove inorganic salts from the product mixture comprising 1,3,4-$(SiMe_3)(C_6F_5)(R)C_5H_3$;
 iii) volatiles are removed from the product mixture under vacuum to give a residue comprising 1,3,4-$(SiMe_3)(C_6F_5)(R)C_5H_3$ as the majority species by weight.

In an embodiment of the invention, the fourth reaction mixture comprising the ligand precursor compound 1,3,4-$(SiMe_3)(C_6F_5)(R)C_5H_3$ is subjected to the following steps:
 i) removing volatiles under vacuum to give a first residue comprising 1,3,4-$(SiMe_3)(C_6F_5)(R)C_5H_3$;
 ii) extracting the first residue into a hydrocarbon give a hydrocarbon solution comprising 1,3,4-$(SiMe_3)(C_6F_5)(R)C_5H_3$;
 iii) filtering the hydrocarbon solution comprising 1,3,4-$(SiMe_3)(C_6F_5)(R)C_5H_3$;

iv) removing volatiles from the filtrate to give a second residue comprising 1,3,4-$(SiMe_3)(C_6F_5)(R)C_5H_3$.

In an embodiment of the invention, the fourth reaction mixture comprising the ligand precursor compound 1,3,4-$(SiMe_3)(C_6F_5)(R)C_5H_3$ is subjected to the following steps:

i) removing volatiles from the fourth reaction mixture under vacuum to give a first residue comprising 1,3,4-$(SiMe_3)(C_6F_5)(R)C_5H_3$;

ii) extracting the first residue with a hydrocarbon solvent to give a hydrocarbon solution comprising 1,3,4-$(SiMe_3)(C_6F_5)(R)C_5H_3$;

iii) filtering the hydrocarbon solution comprising 1,3,4-$(SiMe_3)(C_6F_5)(R)C_5H_3$ to give a filtrate comprising 1,3,4-$(SiMe_3)(C_6F_5)(R)C_5H_3$;

iv) removing volatiles from the filtrate to give a crude product comprising 1,3,4-$(SiMe_3)(C_6F_5)(R)C_5H_3$ as the majority species by weight.

In the present invention, the 1,3,4-$(SiMe_3)(C_6F_5)(R)C_5H_3$ compound may be further isolated or purified by distillation. Distillation which may include vacuum distillation, may be carried out at any time following the formation of the fourth reaction mixture. Preferably, distillation is carried out following work up steps to remove inorganic salts from the fourth reaction mixture and optionally after volatiles have been removed from the fourth reaction mixture under vacuum.

In an embodiment of the invention, the fourth reaction mixture comprising the ligand precursor compound 1,3,4-$(SiMe_3)(C_6F_5)(R)C_5H_3$ is subjected to the following steps:

i) volatiles are removed under vacuum to give a first residue comprising 1,3,4-$(SiMe_3)(C_6F_5)(R)C_5H_3$;

ii) the residue is combined with a hydrocarbon solvent to give a hydrocarbon solution comprising 1,3,4-$(SiMe_3)(C_6F_5)(R)C_5H_3$;

iii) the hydrocarbon solution is subjected to extraction with a weakly acidic aqueous solution and the hydrocarbon solution is retained after phase separation;

iv) volatiles are removed from the hydrocarbon solution under vacuum to give a second residue comprising 1,3,4-$(SiMe_3)(C_6F_5)(R)C_5H_3$;

v) the second residue is distilled under vacuum to give a distillate comprising 1,3,4-$(SiMe_3)(C_6F_5)(R)C_5H_3$.

In an embodiment of the invention, the fourth reaction mixture comprising the ligand precursor compound 1,3,4-$(SiMe_3)(C_6F_5)(R)C_5H_3$ is subjected to the following steps:

i) the fourth reaction mixture is diluted by addition of a hydrocarbon solvent to give a hydrocarbon solution comprising 1,3,4-$(SiMe_3)(C_6F_5)(R)C_5H_3$;

ii) the hydrocarbon solution is subjected to extraction with a weakly acidic aqueous solution and the hydrocarbon solution is retained after phase separation;

iii) volatiles are removed from the hydrocarbon solution under vacuum to give a residue comprising 1,3,4-$(SiMe_3)(C_6F_5)(R)C_5H_3$;

iv) the residue is distilled under vacuum.

In an embodiment of the invention, the fourth reaction mixture comprising the ligand precursor compound 1,3,4-$(SiMe_3)(C_6F_5)(R)C_5H_3$ is subjected to the following steps:

i) the fourth reaction mixture is subjected to extraction with a weakly acidic aqueous solution;

ii) volatiles are removed under vacuum to give a residue comprising 1,3,4-$(SiMe_3)(C_6F_5)(R)C_5H_3$;

iii) the residue is distilled under vacuum.

In an embodiment of the invention, the fourth reaction mixture comprising the ligand precursor compound 1,3,4-$(SiMe_3)(C_6F_5)(R)C_5H_3$ is subjected to the following steps:

i) removing volatiles under vacuum to give a first residue comprising 1,3,4-$(SiMe_3)(C_6F_5)(R)C_5H_3$;

ii) extracting the first residue into a hydrocarbon to give a hydrocarbon solution comprising 1,3,4-$(SiMe_3)(C_6F_5)(R)C_5H_3$;

iii) filtering the hydrocarbon solution comprising 1,3,4-$(SiMe_3)(C_6F_5)(R)C_5H_3$;

iv) removing volatiles from the filtrate to give a second residue comprising 1,3,4-$(SiMe_3)(C_6F_5)(R)C_5H_3$;

v) the second residue is distilled under vacuum to give a distillate comprising 1,3,4-$(SiMe_3)(C_6F_5)(R)C_5H_3$.

The phrases "distilled under vacuum", "vacuum distillation" and the like includes any distillation process carried out at pressures below atmosphere pressure and typically requires distillation head temperatures above ambient temperature. "Ambient temperature" is used interchangeably with "room temperature" and generally includes temperatures in the range of from about 17° C. to about 25° C.

Further Embodiments of the Invention for the Preparation of 1,3,4-$(SiMe_3)(C-_6F_5)(R)C_5H_3$.

In an embodiment of the invention the compound 1,3,4-$(SiMe_3)(C_6F_5)(R)C_5H_3$ is made using the following method, which comprises eight process steps and a single reaction vessel:

i) to 2 molar equivalents of NaCp, 1 eq. $C_6F_6$ is added over >30 min as a solution in THF to give a first reaction mixture which is stirred for >1 hr at at least 40° C.;

ii) 2 eq. of $ClSiMe_3$ are added rapidly (<5 min) in neat form at from 0 to 10° C. to give a second reaction mixture which is stirred for >1 hr at ambient temperature;

iii) 1 eq. NaOtBu is added over 5 min as a solution in THF at 0° C. to give a third reaction mixture which is stirred for at least 1 hr;

iv) 1.5 eq. of RBr is added rapidly in neat form at 0 to 10° C. to give a fourth reaction mixture which is stirred for at least 1 hr;

v) the fourth reaction mixture is diluted with heptane;

vi) the fourth reaction mixture is extracted at least once with saturated aqueous $NH_4Cl$ solution and the organic layer retained;

vii) the volatiles are removed under vacuum to give a first residue comprising 1,3,4-$(SiMe_3)(C_6F_5)(R)C_5H_3$, viii) the first residue is distilled under vacuum to give 1,3,4-$(SiMe_3)(C_6F_5)(R)C_5H_3$ in greater than 40% purity by mole.

In an embodiment of the invention the compound 1,3,4-$(SiMe_3)(C_6F_5)(R)C_5H_3$ is made using the following method, which comprises nine process steps:

i) to 2 molar equivalents of NaCp, 1 eq. $C_6F_6$ is added over >30 min as a solution in THF to give a first reaction mixture which is stirred for >1 hr at at least 40° C.;

ii) the first reaction mixture is added to 2 eq. of $ClSiMe_3$ to give a second reaction mixture which is stirred for >1 hr at ambient temperature;

iii) 1 eq. NaOtBu is added over 5 min as a solution in THF at 0° C. to give a third reaction mixture which is stirred for at least 1 hr;

iv) 1.5 eq. of RBr is added rapidly in neat form at 0 to 10° C. to give a fourth reaction mixture which is stirred for at least 1 hr;

v) volatiles are removed from the fourth reaction mixture under vacuum to give a first residue comprising 1,3,4-$(SiMe_3)(C_6F_5)(R)C_5H_3$, vi) pentane is added to the first residue;

vii) the resulting slurry is extracted at least once with saturated aqueous $NH_4Cl$ solution and the organic layer retained;

viii) the volatiles are removed from the organic layer under vacuum to give a second residue comprising 1,3,4-(SiMe$_3$)(C$_6$F$_5$)(R)C$_5$H$_3$;

ix) the second residue is distilled under vacuum to give 1,3,4-(SiMe$_3$)(C$_6$F$_5$)(R)C$_5$H$_3$ in greater than 40% purity by mole.

In an embodiment of the invention the compound 1,3,4-(SiMe$_3$)(C$_6$F$_5$)(R)C$_5$H$_3$ is made using the following method, which comprises nine process steps:

i) to 1 eq. of NaCp/NaH (1:1 molar ratio), 1 eq. C$_6$F$_6$ is added over >30 min as a solution in THF to give a first reaction mixture which is stirred for >3 hr at least 25° C.;

ii) the first reaction mixture is added to 2 eq. of ClSiMe$_3$ to give a second reaction mixture which is stirred for >1 hr at ambient temperature;

iii) 1 eq. NaOtBu is added over 5 min as a solution in THF at 0° C. to give a third reaction mixture which is stirred for at least 1 hr;

iv) 1.5 eq. of RBr is added rapidly in neat form at 0 to 10° C. to give a fourth reaction mixture which is stirred for at least 1 hr;

v) volatiles are removed from the fourth reaction mixture under vacuum to give a first residue comprising 1,3,4-(SiMe$_3$)(C$_6$F$_5$)(R)C$_5$H$_3$, vi) pentane is added to the first residue;

vii) the resulting slurry is extracted at least once with saturated aqueous NH$_4$Cl solution and the organic layer retained;

viii) the volatiles are removed from the organic layer under vacuum to give a second residue comprising 1,3,4-(SiMe$_3$)(C$_6$F$_5$)(R)C$_5$H$_3$;

ix) the second residue is distilled under vacuum to give 1,3,4-(SiMe$_3$)(C$_6$F$_5$)(R)C$_5$H$_3$ in greater than 40% purity by mole.

In an embodiment of the invention the compound 1,3,4-(SiMe$_3$)(C$_6$F$_5$)(R)C$_5$H$_3$ is made using the following method, which comprises eight process steps and a single reaction vessel:

i) to 1 eq. of NaCp/NaH (1:1 molar ratio), 1 eq. C$_6$F$_6$ is added over >30 min as a solution in THF to give a first reaction mixture which is stirred for >3 hr at least 25° C.;

ii) 2 eq. of ClSiMe$_3$ are added rapidly (<5 min) in neat form at from 0 to 10° C. to give a second reaction mixture which is stirred for >1 hr at ambient temperature;

iii) 1 eq. NaOtBu is added over less than 15 min as a solution in THF at 0° C. to give a third reaction mixture which is stirred for at least 1 hr;

iv) 1.5 eq. of RBr is added rapidly in neat form at 0 to 10° C. to give a fourth reaction mixture which is stirred for at least 1 hr;

v) the fourth reaction mixture is diluted with heptane;

vi) the fourth reaction mixture is extracted at least once with saturated aqueous NH$_4$Cl solution and the organic layer retained;

vii) the volatiles are removed under vacuum to give a first residue comprising 1,3,4-(SiMe$_3$)(C$_6$F$_5$)(R)C$_5$H$_3$;

viii) the first residue is distilled under vacuum to give 1,3,4-(SiMe$_3$)(C$_6$F$_5$)(R)C$_5$H$_3$ in greater than 40% purity by mole.

In an embodiment of the invention the compound 1,3,4-(SiMe$_3$)(C$_6$F$_5$)(R)C$_5$H$_3$ is made using the following method, which comprises 8 process steps and a single reaction vessel:

i) to 2 molar equivalents of NaCp, 1 eq. C$_6$F$_6$ is added over >30 min as a solution in THF to give a first reaction mixture which is stirred for >1 hr at least 40° C.

ii) 2 eq. of ClSiMe$_3$ are added rapidly (<5 min) in neat form at from 0 to 10° C. to give a second reaction mixture which is stirred for >1 hr at ambient temperature iii) 1 eq. NaOtBu is added over less than 15 min as a solution in THF at 0° C. to give a third reaction mixture which is stirred for at least 1 hr;

iv) 1.5 eq. of RBr is added rapidly (<5 min) in neat form at 0 to 10° C. to give a fourth reaction mixture which is stirred for at least 1 hr;

v) the volatiles are removed under vacuum to give a first residue comprising 1,3,4-(SiMe$_3$)(C$_6$F$_5$)(R)C$_5$H$_3$;

vi) 1,3,4-(SiMe$_3$)(C$_6$F$_5$)(R)C$_5$H$_3$ is extracted from the first residue into pentane or heptane to give a hydrocarbon solution comprising 1,3,4-(SiMe$_3$)(C$_6$F$_5$)(R)C$_5$H$_3$;

vii) the hydrocarbon solution comprising 1,3,4-(SiMe$_3$)(C$_6$F$_5$)(R)C$_5$H$_3$ is filtered and the volatiles in the filtrate are removed under vacuum to give a second residue comprising 1,3,4-(SiMe$_3$)(C$_6$F$_5$)(R)C$_5$H$_3$;

viii) the second residue is distilled under vacuum to give 1,3,4-(SiMe$_3$)(C$_6$F$_5$)(R)C$_5$H$_3$ in greater than 40% purity by mole.

In an embodiment of the invention the compound 1,3,4-(SiMe$_3$)(C$_6$F$_5$)(R)C$_5$H$_3$ is made using the following method, which comprises eight process steps and a single reaction vessel:

i) to 1 eq. of NaCp/NaH (1:1 molar ratio), 1 eq. C$_6$F$_6$ is added over >30 min as a solution in THF to give a first reaction mixture which is stirred for >3 hr at at least 25° C.

ii) 2 eq. of ClSiMe$_3$ are added rapidly (<5 min) in neat form at from 0 to 10° C. to give a second reaction mixture which is stirred for >1 hr at ambient temperature iii) 1 eq NaOtBu is added over less than 15 min as a solution in THF at 0° C. to give a third reaction mixture which is stirred for ca. 1 hr;

iv) 1.5 eq. of RBr is added rapidly in neat form at 0 to 10° C. to give a fourth reaction mixture which is stirred for at least 1 hr;

v) the volatiles are removed under vacuum to give a first residue comprising 1,3,4-(SiMe$_3$)(C$_6$F$_5$)(R)C$_5$H$_3$;

vi) 1,3,4-(SiMe$_3$)(C$_6$F$_5$)(R)C$_5$H$_3$ is extracted from the first residue into pentane or heptane to give a hydrocarbon solution comprising 1,3,4-(SiMe$_3$)(C$_6$F$_5$)(R)C$_5$H$_3$;

vii) the hydrocarbon solution comprising 1,3,4-(SiMe$_3$)(C$_6$F$_5$)(R)C$_5$H$_3$ is filtered and the volatiles in the filtrate are removed under vacuum to give a second residue comprising 1,3,4-(SiMe$_3$)(C$_6$F$_5$)(R)C$_5$H$_3$;

viii) the second residue is distilled under vacuum to give 1,3,4-(SiMe$_3$)(C$_6$F$_5$)(R)C$_5$H$_3$ in greater than 40% purity by mole.

The purity of the ligand precursor compound 1,3,4-(SiMe$_3$)(C$_6$F$_5$)(R)C$_5$H$_3$ can be determined by techniques well known in the art such as by way of example only, gas chromatography with mass spectrum detection (GC-MS) or by nuclear magnetic resonance (NMR) methods.

Ligand Metallation.

The compound 1,3,4-(SiMe$_3$)(C$_6$F$_5$)(R)C$_5$H$_3$ is preferably employed as a ligand precursor, which on reaction with a suitable transitional metal species becomes ligated to a metal center (i.e. a bond is formed between at least one atom, preferably a carbon atom, of the ligand and the metal).

In an embodiment of the invention, 1,3,4-(SiMe$_3$)(C$_6$F$_5$)(R)C$_5$H$_3$ is reacted with a group 4 transition metal chloride M*X*$_4$ to give (1,2-(C$_6$F$_5$)(R)C$_5$H$_3$)$_n$M*X*$_{4-n}$, where M* is Ti, Zr, or Hf; X* is a halide; n is 1-4; and R is as defined above.

In an embodiment of the invention, 1,3,4-(SiMe$_3$)(C$_6$F$_5$)(R)C$_5$H$_3$ is reacted with a group 4 transition metal chloride M*X*$_4$ to give (1,2-(C$_6$F$_5$)(R)C$_5$H$_3$)$_n$M*X*$_{4-n}$, where M* is Ti, Zr, or Hf; X* is a halide; n is 1 or 2; and R is as defined above.

In an embodiment of the invention, 1,3,4-(SiMe$_3$)(C$_6$F$_5$)(R)C$_5$H$_3$ is reacted with a group 4 transition metal chloride M*X*$_4$ to give (1,2-(C$_6$F$_5$)(R)C$_5$H$_3$)M*X*$_3$ having the structure VI, where M* is Ti, Zr, or Hf; X* is a halide; and R is as defined above.

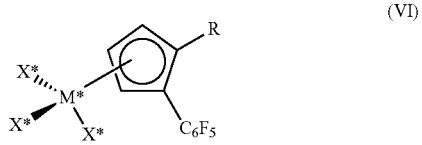

(VI)

In an embodiment of the invention, 1,3,4-(SiMe$_3$)(C$_6$F$_5$)(R)C$_5$H$_3$ is reacted with a group 4 transition metal chloride M*X*$_4$ in the presence of a hydrocarbon solvent to give a mixture comprising (1,2-(C$_6$F$_5$)(R)C$_5$H$_3$)M*X*$_3$, where M* is Ti, Zr, or Hf; X* is a halide; and R is as defined above.

In an embodiment of the invention, 1,3,4-(SiMe$_3$)(C$_6$F$_5$)(R)C$_5$H$_3$ contaminated with 1,3,5-(SiMe$_3$)(C$_6$F$_5$)(R)C$_5$H$_3$ is reacted with a group 4 transition metal chloride M*X*$_4$ in the presence of a hydrocarbon solvent to give after filtration and extraction steps (1,2-(C$_6$F$_5$)(R)C$_5$H$_3$)M*X*$_3$, where M* is Ti, Zr, or Hf; X* is a halide; and R is as defined above. Filtration and subsequent washing/extraction with hydrocarbons (e.g. pentane, heptane, etc.) removes metallated product arising from the 1,3,5-(SiMe$_3$)(C-$_6$F$_5$)(R)C$_5$H$_3$ regioisomer present as a contaminant in 1,3,4-(SiMe$_3$)(C$_6$F$_5$)(R)C$_5$H$_3$, due to the much higher solubility of (1,3-(C$_6$F$_5$)(R)C$_5$H$_3$)M*X*$_3$ in hydrocarbon solvents.

In an embodiment of the invention, 1,3,4-(SiMe$_3$)(C$_6$F$_5$)(R)C$_5$H$_3$C$_5$H$_3$ contaminated with 1,3,5-(SiMe$_3$)(C$_6$F$_5$)(R)C$_5$H$_3$ is reacted with a group 4 transition metal chloride M*X*$_4$ in heptane (or other suitable hydrocarbon) to give after filtration and extraction steps a compound having the formula (1,2-(C$_6$F$_5$)(R)C$_5$H$_3$)M*X*$_3$ in greater than about 85 mol % purity, where M* is Ti, Zr, or Hf; X* is a halide; and R is as defined above. Filtration and subsequent washing/extraction with heptane or pentane removes metallated product arising from the 1,3,5-(SiMe$_3$)(C$_6$F$_5$)(R)C$_5$H$_3$ regioisomer present as a contaminant in 1,3,4-(SiMe$_3$)(C$_6$F$_5$)(R)C$_5$H$_3$, due to the much higher solubility of (1,3-(C$_6$F$_5$)(R)C$_5$H$_3$)M*X*$_3$ in hydrocarbon solvents.

In an embodiment of the invention, a distillate comprising 1,3,4-(SiMe$_3$)(C-$_6$F$_5$)(R)C$_5$H$_3$ is reacted with a group 4 transition metal chloride M*X*$_4$ in the presence of a hydrocarbon solvent to give a mixture comprising (1,2-(C$_6$F$_5$)(R)C$_5$H$_3$)M*X*$_3$, where M* is Ti, Zr, or Hf; X* is a halide; and R is as defined above.

In an embodiment of the invention, a distillate comprising 1,3,4-(SiMe$_3$)(C-$_6$F$_5$)(R)C$_5$H$_3$ in at least 40 mol % purity is reacted with a group 4 transition metal chloride M*X*$_4$ in the presence of a hydrocarbon solvent to give a mixture comprising (1,2-(C-$_6$F$_5$)(R)C$_5$H$_3$)M*X*$_3$, where M* is Ti, Zr, or Hf; X* is a halide; and R is as defined above.

In an embodiment of the invention, a distillate comprising 1,3,4-(SiMe$_3$)(C-$_6$F$_5$)(R)C$_5$H$_3$ in at least 40 mol % purity is reacted with a group 4 transition metal chloride M*X*$_4$ in the presence of a hydrocarbon solvent to give a mixture comprising (1,2-(C-$_6$F$_5$)(R)C$_5$H$_3$)M*X*$_3$, where M* is Ti, Zr, or Hf; X* is a halide; and R is as defined above, and wherein (1,2-(C$_6$F$_5$)(R)C$_5$H$_3$)M*X*$_3$ is isolated from the mixture in greater than 85 mol % purity by collection from the mixture by filtration, followed by washing with a hydrocarbon solvent.

In an embodiment of the invention, a distillate comprising 1,3,4-(SiMe$_3$)(C-$_6$F$_5$)(R)C$_5$H$_3$ is reacted with a group 4 transition metal chloride M*X*$_4$ in heptane (or other suitable hydrocarbon) to give after filtration and extraction steps a compound having the formula (1,2-(C$_6$F$_5$)(R)C$_5$H$_3$)M*X*$_3$ in greater than about 85 mol % purity, where M* is Ti, Zr, or Hf; X* is a halide; and R is as defined above.

In an embodiment of the invention, a distillate comprising 1,3,4-(SiMe$_3$)(C-$_6$F$_5$)(R)C$_5$H$_3$ in at least 40 mol % purity is reacted with a group 4 transition metal chloride M*X*$_4$ in heptane (or other suitable hydrocarbon) to give after filtration and extraction steps a compound having the formula (1,2-(C$_6$F$_5$)(R)C$_5$H$_3$)M*X*$_3$ in greater than about 85 mol % purity, where M* is Ti, Zr, or Hf; X* is a halide; and R is as defined above.

In an embodiment of the invention the compound having the formula (1,2-(C-$_6$F$_5$)(R)C$_5$H$_3$)M*X*$_3$ is reacted with a phosphinimine compound defined by the formula: [R*$_3$P=N][M$^4$] to give a phosphinimine catalyst (1,2-(C$_6$F$_5$)(R)C$_5$H$_3$)(R*$_3$P=N)M*X*$_2$ with the structure VII,

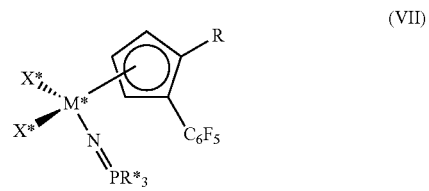

(VII)

wherein each R* is independently selected from the group consisting of a hydrogen atom; a halogen atom; C$_{1-20}$ hydrocarbyl radicals which are unsubstituted by or further substituted by one or more halogen atom; C$_{1-20}$ alkyl radical; C$_{1-8}$ alkoxy radical; C$_{6-10}$ aryl or aryloxy radical; amido radical; silyl radical; and germanyl radical; and where M$^4$ is Na$^+$, Li$^+$ or K$^+$; M* is Ti, Zr or Hf; X* is a halide; and R is defined as above.

In an embodiment of the invention the compound having the formula (1,2-(C-$_6$F$_5$)(R)C$_5$H$_3$)M*X*$_3$ is reacted with a phosphinimine compound defined by the formula: R*$_3$P=N—SiMe$_3$ to give a phosphinimine catalyst (1,2-(C$_6$F$_5$)(R)C$_5$H$_3$)(R*$_3$P=N)M*X*$_2$ with the structure VII, where each R* is independently selected from the group consisting of a hydrogen atom; a halogen atom; C$_{1-20}$ hydrocarbyl radicals which are unsubstituted by or further substituted by one or more halogen atom; C$_{1-20}$ alkyl radical; C$_{1-8}$ alkoxy radical; C$_{6-10}$ aryl or aryloxy radical; amido radical; silyl radical; and germanyl radical; M* is Ti, Zr or Hf; X* is a halide; and R is defined as above.

In an embodiment of the invention the compound 1,3,4-(SiMe$_3$)(C$_6$F$_5$)(R)C$_5$H$_3$ is reacted with a group 4 transition metal chloride already comprising a phosphinimine ligand (R*$_3$P=N)M*X*$_3$, to give a phosphinimine catalyst (1,2-(C$_6$F$_5$)(R)C$_5$H$_3$)(R*$_3$P=N)M* X*$_2$ with the structure VII, where each R* is independently selected from the group consisting of a hydrogen atom; a halogen atom; C$_{1-20}$ hydrocarbyl radicals which are unsubstituted by or further substituted by one or more halogen atom; C$_{1-20}$ alkyl radical; C$_{1-8}$ alkoxy radical; C$_{6-10}$ aryl or aryloxy radical; amido radical; silyl radical; and germanyl radical; M* is Ti, Zr or Hf; X* is a halide; and R is defined as above.

In an embodiment of the invention a distillate comprising 1,3,4-(SiMe$_3$)(C$_6$F$_5$)(R)C$_5$H$_3$ in at least 40 mol % purity is combined with (R*$_3$P=N)M*X*$_3$ in the presence of a hydrocarbon solvent to give a mixture comprising (1,2-(C$_8$F$_5$)(R)C$_5$H$_3$)(R*$_3$P=N)M* X*$_2$ with the structure VII, where each R* is independently selected from the group consisting of a hydrogen atom; a halogen atom; C$_{1-20}$ hydrocarbyl radicals which are unsubstituted by or further substituted by one or more halogen atom; C$_{1-20}$ alkyl radical; C$_{1-8}$ alkoxy radical; C$_{6-10}$ aryl or aryloxy radical; amido radical; silyl radical; and germanyl radical; M* is Ti, Zr or Hf; X* is a halide; and R is defined as above.

In an embodiment of the invention, the metallation reaction is carried out in toluene.

In an embodiment of the invention, the metallation reaction is carried out in hydrocarbon solvent such as heptane.

In an embodiment of the invention, the metallation reaction is carried out at elevated temperature, for example at about 40° C. to 90° C. in a hydrocarbon having a suitable corresponding boiling point.

In an embodiment of the invention, reaction of the compound ((1,2-(C$_6$F$_5$)(R)C$_5$H$_3$)M*X*$_3$ with a phosphinimine compound to give a phosphinimine catalyst is carried out in toluene, where R, M* and X* are defined as above.

In an embodiment of the invention, reaction of the compound ((1,2-(C$_6$F$_5$)(R)C$_5$H$_3$Cp)M*X*$_3$ with a phosphinimine compound to give a phosphinimine catalyst is carried out at elevated temperature, for example at about 40° C. to 90° C., where R, M* and X* are defined as above.

EXAMPLES

General Conditions: All reactions involving air and or moisture sensitive compounds were conducted under nitrogen using standard Schlenk techniques, or in a glovebox. Toluene and heptane were purified using the system described by Pangborn, Grubbs, et. al. in Pangborn, A. B; Giardello, M. A.; Grubbs, R. H; Rosen, R. K.; Timmers, F. J. *Organometallics* 1996, 15, 1518. Tetrahydrofuran was purified by passing it through a column of activated alumina, and pentane and the other solvents were stored over activated 4 Å sieves. All chemicals were purchased from Aldrich and used without further purification, with the exception of hexafluorobenzene and 1-bromopropane which were dried over CaH$_2$ and filtered prior to use. Deuterated solvents were purchased from CIL (chloroform-d, toluene-d$_8$) and were stored over 4 Å sieves. NMR spectra were recorded on Bruker spectrometers (200 and 400.1 MHz for $^1$H, 162 MHz for $^{31}$P, 376 MHz for $^{19}$F). GC-MS analysis was accomplished using an HP GC 6890 (50 kPa constant pressure UHP He carrier gas @ 50° C.) equipped with a ZB-5MS (5% phenyl methyl siloxane) column (30 m length×0.25 mm i.d.×1 μm film thickness). The detectors used were a HP 5973 Mass Selective Detector and FID detector. The temperature program on the GC was as follows: initial temp 50° C., initial time 5 min; rate 10° C./min; final temp. 300° C.; final time 15 min; run time 45 min; inlet split ratio 100:1; inlet temperature 275° C. FID detector: temp 310° C.; hydrogen 35 mL/min; air 350 mL/min; nitrogen make-up 25 mL/min.

Synthesis of 1,3,4-(SiMe$_3$)(C$_6$F$_5$)(n-Pr)C$_5$H$_3$

Example 1

Inventive

Synthesis of a reaction mixture comprising 1,3,4-(SiMe$_3$)(C$_6$F$_5$)(n-Pr)C$_5$H$_3$: Step 1) NaH (4.9 g, 204 mmol) was weighed into a 2 liter round bottomed flask with a large stir bar. NaC$_5$H$_5$ (2.0 M in THF, 100 mL, 200 mmol) and THF (300 mL) was added into the flask. The contents were stirred while the flask was placed in an oil bath. Next, C$_6$F$_6$ (37.21 g, 200 mmol) was added to the slurry over about 10 minutes. A purple color developed and gas evolution was observed. The reaction temperature went from 27° C. to about 52° C. The reaction mixture was stirred at 40° C. overnight and was then cooled to room temperature. Step 2) ClSiMe$_3$ (2.05×200 mmol=410 mmol) was poured into the flask. A temperature increase from 27° C. to 31° C. was observed. The reaction was stirred at room temperature overnight. The head space of the reaction was purged with nitrogen to remove any Me$_3$SiF. Step 3) The reaction mixture obtained in step 2 was cooled to 0° C. and n-BuLi (1.6M in hexanes, 125 mL, 200 mmol) was added carefully (dropwise) to the reaction flask over 1.5 hours while the reaction temperature was controlled at 3.5-7.5° C. During the addition of the n-BuLi solution, a very vigorous reaction with large temperature excursion was observed. After the addition of nBuLi, the reaction mixture was stirred for additional 10 minutes at 0° C. Step 4) n-Propyl bromide (300 mmol) was poured to the reaction mixture at 0° C. No obvious reaction temperature increase was observed. The reaction temperature was maintained below 12° C. for 1 hour and was then allowed to increase to room temperature naturally for the next 3 hours. At this time a few drops of the product mixture was added to a diethyl ether/saturated NH$_4$Cl aqueous solution. After quick mixing, the diethyl ether solution was subjected to GC-MS analysis. The data shown in Table 2, summarizes the GC-MS results.

TABLE 2

Analysis (GCMS) of the Reaction Mixture Obtained after nPrBr Addition

| M+ | Assignment | Retention time (min) | Content (mol %) |
|---|---|---|---|
| 138 | (Me$_3$Si)C$_5$H$_5$ | 11.1 | 4.05 |
| 180 | Not assigned | 16.6 | 3 |
| 210 | Not assigned | 16.8 | 2.19 |
| 232 | (C$_6$F$_5$)C$_5$H$_5$ | 18 | 11.03 |
| 274 | (C$_6$F$_5$)(nPr)C$_5$H$_4$ | 20.21 | 6.45 |
| 274 | (C$_6$F$_5$)(nPr)C$_5$H$_4$ | 22.55 | 8.22 |
| 346 | 1,3,4-(SiMe$_3$)(C$_6$F$_5$)(n-Pr)C$_5$H$_3$ | 23.45 | 44.46 |
| 346 | 1,3,5-(SiMe$_3$)(C$_6$F$_5$)(n-Pr)C$_5$H$_3$ | 24.6 | 8.49 |
| 388 | (SiMe$_3$)(C$_6$F$_5$)(n-Pr)$_2$C$_5$H$_2$ | 25.3 | 7.21 |
| 388 | (SiMe$_3$)(C$_6$F$_5$)(n-Pr)$_2$C$_5$H$_2$ | 24.62 | 4.91 |

As can be seen from the data in Table 2, the crude product contains as the majority species 1,3,4-(SiMe$_3$)(C$_6$F$_5$)(n-Pr)C$_5$H$_3$ at over 40 mol %, and further that less than 10 mol % of the undesired 1,3,5-(SiMe$_3$)(C$_6$F$_5$)(n-Pr)C$_5$H$_3$ species is present.

Workup of reaction mixture comprising 1,3,4-(SiMe$_3$)(C$_6$F$_5$)(n-Pr)C$_5$H$_3$: The product mixture was placed under vacuum pressure to remove volatile components. The resulting residue was then extracted with pentane and was filtered. The pentane was removed under vacuum and the resulting residue was distilled under vacuum pressure. A fraction (34.66 g) obtained at temperatures of 58-85° C. under 300 microns of vacuum pressure was collected. GCMS showed that after distillation the desired 1,3,4-(SiMe$_3$)(C$_6$F$_5$)(n-Pr)C$_5$H$_3$ (M+=346) was present in greater than 50 mol percent. The present inventive example is further illustrated in Reaction Scheme 1.

Reaction Scheme 1:

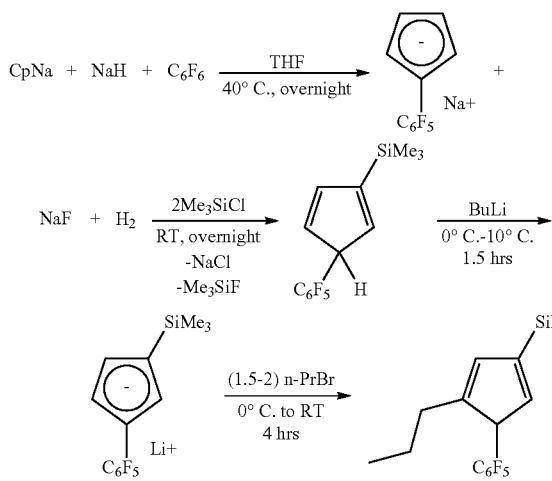

Example 2

Comparative

This example was carried out at a 20 mmol reaction scale (relative to the starting $C_6F_6$ material) using a procedure analogous to that described above for Inventive Example 1, but only one molar equivalent of $Me_3SiCl$ was used in step 2. GSMS of the third reaction mixture obtained in step 4 contained almost none of the desired product 1,3,4-$(SiMe_3)$$(C_6F_5)(n$-$Pr)C_5H_3$ (M+=346 at retention time 23.45 min). Hence, it is an essential feature of the present invention that at least 2 molar equivalents of $Me_3SiCl$ be used in step 2 of the synthesis.

Example 3

Inventive

Synthesis of a reaction mixture comprising 1,3,4-$(SiMe_3)$$(C_6F_5)(n$-$Pr)C_5H_3$: For this example a procedure similar to Example 1 was employed but with the following modifications: 50 mmols of $C_6F_6$ was added dropwise in 3 hours to a flask containing NaCp (50 mmols, 2M, 25 mL in THF) and NaH (50 mmols, 1.2 g) at 65° C. The flask was fit with a condenser to prevent evaporation of $C_6F_6$. After the addition, the reaction was let proceed at 65° C. for 1 more hour and was cooled to room temperature. $Me_3SiCl$ (102.5 mmols, 2.05 molar equivalents) was quickly added to the reaction flask. The content was stirred for 1 hour at room temperature and was further reacted at 50° C. for 3 hours. The content was cooled to 0° C. and NaOtBu (50 mmols, 4.8 g in 30 mL of THF) was added in 15 minutes. After the reaction was stirred for 5 minutes, nPrBr (75 mmols, 9.2 g) was added to the reaction. The reaction was stirred at 0° C. for 3 hours at room temperature for 1 hour. GC-MS results for the crude product are summarized in Table 3.

TABLE 3

Analysis (GCMS) of the Reaction Mixture Obtained after nPrBr Addition

| M+ | Assignment | Retention time (min) | Content (mol %) |
|---|---|---|---|
| 138 | $(Me_3Si)C_5H_5$ | 11.1 | 3.30 |
| 142 | Not assigned | 14.9 | 1.03 |
| 180 | Not assigned | 16.6 | 1.6 |
| 210 | Not assigned | 16.8 | 1.9 |
| 232 | $(C_6F_5)C_5H_5$ | — | 0 |
| 274 | $(C_6F_5)(nPr)C_5H_4$ | — | 0 |
| 274 | $(C_6F_5)(nPr)C_5H_4$ | — | 0 |
| 304 | $(Me_3Si)(C_6F_5)C_5H_4$ | 21.9 | 4.7 |
| 346 | 1,3,4-$(SiMe_3)(C_6F_5)(n$-$Pr)C_5H_3$ | 23.45 | 50.4 |
| 346 | 1,3,5-$(SiMe_3)(C_6F_5)(n$-$Pr)C_5H_3$ | 24.6 | 14.2 |
| 376 | $(SiMe_3)_2(C_6F_5)C_5H_3$ | 24.82 | 10.4 |
| 388 | $(SiMe_3)(C_6F_5)(n$-$Pr)_2C_5H_2$ | 25.3 | 7.1 |
| 388 | $(SiMe_3)(C_6F_5)(n$-$Pr)_2C_5H_2$ | 24.62 | 5.4 |

As can be seen from the data in Table 3, the crude product contains as the majority species, 1,3,4-$(SiMe_3)(C_6F_5)(n$-$Pr)C_5H_3$ at over 50 mol %, which is even higher than that observed in Example 1. Hence the use of a sodium alkoxide base (e.g. NaOtBu) in place of the more aggressive alkyl lithium base (e.g. nBuLi) provides for higher yield of the desired product. It also reduced the exotherm experienced during step 3 of the synthesis. A reduction in reaction exotherm is particularly important if the synthesis is to be increased in scale (see Inventive Example 4 below). The 1,3,5-$(SiMe_3)(C_6F_5)(n$-$Pr)C_5H_3$ species is present in about 14 mol %, while the decomposition product $(C_6F_5)(nPr)C_5H_4$ which arises from desilylation reactions is now completely absent (no peak is observed at M+=274 in the GC-MS). The present inventive example is further illustrated in Reaction Scheme 2.

Reaction Scheme 2:

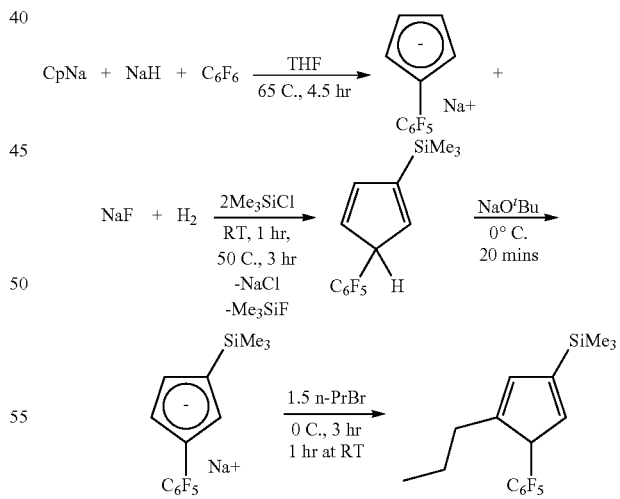

Example 4

Inventive, Large Scale

Synthesis of a reaction mixture comprising 1,3,4-$(SiMe_3)$$(C_6F_5)(n$-$Pr)C_5H_3$: The present example employed the same procedures as in Example 3 but at a 500 mmol reaction scale (relative to the $C_6F_6$ starting material). NaOtBu (49.54 g, 500 mmols with 97% purity accounted) in THF (200 mL) was used in step 3. The addition of the THF solution of NaOtBu took ca. 45 minutes at 3° C. to 4° C. and without any significant temperature excursion being observed. After the addition of nPrBr to the reaction at 0° C., the reaction was warmed to room temperature in 3 hours (note: a small reaction exotherm was observed during this alkylation step) and let proceed at room temperature for 1.5 hours. GC-MS results of the crude product (after hydrolysis with a $NH_4Cl$ aqueous solution) are summarized in Table 4.

TABLE 4

Analysis (GCMS) of the Reaction Mixture Obtained after nPrBr Addition

| M+ | Assignment | Retention time (min) | Content (mol %) |
|---|---|---|---|
| 138 | $(Me_3Si)C_5H_5$ | 11.1 | 4.6 |
| 142 | Not assigned | 13.9 | 4.0 |
| 132 | Dicyclopentadiene | 14.8 | 1.2 |
| 210 | Not assigned | 16.8 | 1.8 |
| 245 | Not assigned | 20.3 | 1.8 |
| 274 | $(C_6F_5)(nPr)C_5H_4$ | — | 0 |
| 274 | $(C_6F_5)(nPr)C_5H_4$ | — | 0 |
| 304 | Not assigned | 21.9 | 2.9 |
| 346 | $1,3,4-(SiMe_3)(C_6F_5)(n-Pr)C_5H_3$ | 23.45 | 47 |
| 346 | $1,3,5-(SiMe_3)(C_6F_5)(n-Pr)C_5H_3$ | 24.6 | 12 |
| 376 | $(SiMe_3)_2(C_6F_5)C_5H_3$ | 24.82 | 9.6 |
| 388 | $(SiMe_3)(C_6F_5)(n-Pr)_2C_5H_2$ | 25.3 | 8.9 |
| 388 | $(SiMe_3)(C_6F_5)(n-Pr)_2C_5H_2$ | 24.62 | 6.1 |

As can be seen from the data in Table 4, the crude product contains as the majority species, $1,3,4-(SiMe_3)(C_6F_5)(n-Pr)C_5H_3$ at over 45 mol %, which is similar to that obtained at a smaller scale (compare Inventive examples 3 and 4). Hence the present invention demonstrates the practicality of the inventive synthetic method at large scale (e.g. 500 mmol). Further the use of a sodium alkoxide base (e.g. NaOtBu) in place of the more aggressive alkyl lithium base (e.g. nBuLi) reduced the exotherm experienced during step 3 of the synthesis, which is important for large scale reactions. Inventive examples 3 and 4 are also similar in terms of the amount of undesirable species that are formed, again showing the scaleability of the present synthesis. A $1,3,5-(SiMe_3)(C_6F_5)(n-Pr)C_5H_3$ species is present in about 12 mol %, while the decomposition product $(C_6F_5)(nPr)C_5H_4$ which arises from desilylation reactions remains absent (no peak is observed at M+=274 in the GC-MS).

Workup of reaction mixture comprising $1,3,4-(SiMe_3)(C_6F_5)(n-Pr)C_5H_3$: The crude reaction mixture comprising the $1,3,4-(SiMe_3)(C_6F_5)(n-Pr)C_5H_3$ was pumped under vacuum to remove volatiles. Pentane (200 mL) was added to the resulting residue to give a slurry. A saturated $NH_4Cl$ aqueous solution (200 mL) was added and the slurry was vigorously mixed. The organic layer was separated and was subjected to a vacuum pressure to remove volatiles. The resulting residue was subjected to vacuum distillation. A fraction (95.6 g) was obtained at temperatures of from 53-91° C. (distillation head temperature) under a pressure range of 500 to 400 mTorr. GC-MS showed that after distillation the desired $1,3,4-(SiMe_3)(C_6F_5)(n-Pr)C_5H_3$ (M+=346) was present in 57 mol % purity. The overall yield of $1,3,4-(SiMe_3)(C_6F_5)(n-Pr)C_5H_3$ based on $C_6F_6$ was 31%.

Example 5

Speed of $Me_3SiCl$ Addition

This example was carried out using the same procedures described above in Inventive Example 4, except that in Step 2, $Me_3SiCl$ was added to the first reaction mixture slowly (over 36 minutes). In this case, the crude product mixture contained 16.2% of the by-product $(SiMe_3)_2(C_6F_5)C_5H_3$ (GC-MS shows M+=376 in 16.2 mol %) compared to 9.6 mol % of the by-product $(SiMe_3)_2(C_6F_5)C_5H_3$ obtained in Example 4. Hence, this example demonstrates that is may be preferably to add $Me_3SiCl$ to the second reaction mixture quickly, in order to minimize the amount of $(SiMe_3)_2(C_6F_5)C_5H_3$ formed. Alternatively, this example further shows that it may be preferable that the first reaction mixture obtained in step 1 be added to at least 2 molar equivalents of $Me_3SiCl$, rather than in the reverse order, to ensure that the $Me_3SiCl$ stays in excess at all times.

Example 6

Inventive-"One Pot" Preparation of $1,3,4-(SiMe_3)(C_6F_5)(n-Pr)C_5H_3$ with Aqueous Workup Synthesis of a reaction mixture comprising $1,3,4-(SiMe_3)(C-_6F_5)(n-Pr)C_5H_3$: Step 1) To a THF solution (50 mL) of $NaC_5H_5$ (92.8 g of 2 M solution in THF, 200 mmol) at 60° C. was added a THF solution (10 mL) of $C_6F_6$ (18.6 g, 100 mmol) over 45-60 min. The resulting dark purple solution was stirred at 60° C. for 4 hours. Step 2) The reaction mixture obtained in step 1 was cooled to between 0-10° C. and neat $ClSiMe_3$ (21.7 g, 200 mmol) was added in a single batch. The resulting reaction mixture was allowed to warm slowly to ambient temperature over 16-18 hours (overnight). Step 3) To the resulting pale brown slurry was added a THF solution (50 mL) of NaOtBu (9.6 g, 100 mmol) dropwise over 5-10 min and the dark brown slurry was stirred at between 0-10° C. for 1 hour. Step 4) After ensuring that the slurry was cooled to 0° C., neat 1-bromopropane (18.45 g, 150 mmol) was added in a single batch and the mixture was stirred at 0° C. for 4 hours. After warming to around ambient temperature, the slurry was diluted with heptane (400 mL) and saturated aqueous $NH_4Cl$ (200 mL) was added with vigorous stirring. Stirring was stopped and the bottom aqueous layer was siphoned from the mixture by cannula. A second portion of $NH_4Cl$ solution (200 mL) was added with stirring and the bottom layer again removed by cannula. The combined heptane/THF organic layer was concentrated under vacuum to give the crude product as a dark liquid (28.6 g) which was subjected to vacuum distillation. A volatile fraction (2.3 g; bath temp. 30-80° C.; still head temp. 35-43° C.; pressure 700-800 mTorr) was collected and discarded. The second fraction, a pale yellow oil (20.8 g; bath temp. 96-130° C.; still head temp. 44-72° C.; pressure 400 mTorr), was collected and determined by GCMS (see Table 5) to have a purity of 58.6 mol % for $1,3,4-(SiMe_3)(C_6F_5)(n-propyl)C_5H_3$ (m/z=346; $t_R$=23.4 min).

Example 7

Inventive-Large Scale Preparation of $1,3,4-(SiMe_3)(C_6F_5)(n-Pr)C_5H_3$ with Non-Aqueous Workup Step 1) To a THF suspension (600 mL) of NaH (12.0 g, 500 mmol) and $NaC_5H_5$ (234.5 g of 2 M solution in THF, 500 mmol) at ambient temperature was added a THF solution (50 mL) of $C_6F_6$ (93.0 g, 500 mmol) over 45-60 min. The resulting dark purple solution was heated to 40° C. and stirred for 16-18 hours (overnight). Step 2) After cooling the mixture to ambient temperature, neat $ClSiMe_3$ (109.2 g, 1005 mmol) was then added in a single batch and the reaction mixture was stirred for 16-18 hours (overnight). Step 3) To the resulting pale brown slurry cooled to 0° C. was added a THF solution (300 mL) of NaOtBu (49.5 g, 515 mmol) dropwise over around 2.5 hours and the dark brown slurry was stirred at between 0-10° C. for 1 hour. Step 4) After ensuring that the slurry was cooled to 0° C., neat 1-bromopropane (92.2 g, 750 mmol) was added in a single batch and the mixture was allowed to warm slowly to between 10-15° C., over 4 hours. After warming to around ambient temperature, the volatiles were removed under vacuum and the residue was slurried in pentane (800 mL). The slurry was filtered through a sintered glass frit and the filter cake was washed with additional pentane until the filtrate was colourless. The combined pentane filtrate was concentrated under vacuum to give the crude product as a dark liquid (110.7 g) which was subjected to vacuum distillation. A volatile fraction (9.85 g; bath temp. 30-92° C.; still head temp. 26-48° C.; pressure 1000 down to 500 mTorr) was collected and discarded. The second fraction, a pale yellow oil (83.8 g; bath temp. 120-144° C.; still head temp. 72-86° C.; pressure 500 down to 300 mTorr), was collected and determined by GCMS (see Table 6) to have a purity of 52.7 mol % 1,3,4-$(SiMe_3)(C_6F_5)$(n-propyl)$C_5H_3$ (m/z=346; $t_R$=23.4 min).

TABLE 5

Analysis (GCMS) of Crude Product after Aqueous Work-Up and after Distillation

| m/z (FW) | Assignment | Crude product after aqueous work-up; 29.2 g | | Distilled product; 20.8 g | |
|---|---|---|---|---|---|
| | | GC area % (mol %) | Calcd. wt. of products (g) | GC area % (mol %) | Calcd. wt. of products (g) |
| 66 | Cyclopentadiene, $C_5H_6$ | 9.9 | 0.72 | | |
| 186 | $C_6F_6$ | 1.8 | 0.37 | | |
| 138 | $(Me_3Si)C_5H_5$ | 17.7 | 2.70 | | |
| 132 | dicyclopentadiene | 2.9 | 0.42 | | |
| 210 | Not assigned | 1.1 | 0.26 | | |
| 232 | $(C_6F_5)C_5H_5$ | 8.9 | 2.28 | 4.7 | 0.66 |
| 274 | $(C_6F_5)(nPr)C_5H_4$ | 1 | 0.30 | 1.0 | 0.16 |
| 304 | $(Me_3Si)(C_6F_5)C_5H_4$ | 2 | 0.67 | 4.0 | 0.73 |
| 274 | $(C_6F_5)(nPr)C_5H_4$ | 1.3 | 0.39 | 1.5 | 0.25 |
| 398 | $(C_6F_5)_2C_5H_4$ | 1.9 | 0.84 | 3.2 | 0.77 |
| 346 | 1,3,4-$(SiMe_3)(C_6F_5)$(n-Pr)$C_5H_3$ | 33.8 | 12.92 | 58.6 | 12.19 |
| 346 | 1,3,5-$(SiMe_3)(C_6F_5)$(n-Pr)$C_5H_3$ | 6.9 | 2.64 | 12.3 | 2.56 |
| 388 | $(SiMe_3)(C_6F_5)$(n-Pr)$_2C_5H_2$ | 5 | 2.14 | 7.5 | 1.75 |
| 388 | $(SiMe_3)(C_6F_5)$(n-Pr)$_2C_5H_2$ | 3.5 | 1.50 | 5.3 | 1.24 |
| 388 | $(SiMe_3)(C_6F_5)$(n-Pr)$_2C_5H_2$ | 0.7 | 0.30 | 0.8 | 0.19 |
| 398 | $(C_6F_5)_2C_5H_4$ | 1.6 | 0.70 | 1.2 | 0.29 |
| Yield of regioisomeric $(SiMe_3)(C_6F_5)$(n-Pr)$C_5H_3$ species | | 15.6 g/45% | | 14.8 g/43% | |
| Yield of 1,3,4-$(SiMe_3)(C_6F_5)$(n-Pr)$C_5H_3$ | | 12.9 g/37% | | 12.2 g/35% (based on 100 mmol $C_6F_6$) | |
| Ratio of 1,3,4/1,3,5 regioisomers | | 4.9:1 | | 4.8:1 | |

TABLE 6

Analysis (GCMS) of Crude Product after Filtration Work-Up and after Distillation

| m/z (FW) | Assignment | Crude product after filtration work-up; 110.7 g | | Distilled product; 83.8 g | |
|---|---|---|---|---|---|
| | | GC area % (mol %) | Calcd. wt. of products (g) | GC area % (mol %) | Calcd. wt. of products (g) |
| 138 | $(Me_3Si)C_5H_5$ | 6.3 | 2.9 | | |
| 132 | dicyclopentadiene | 1.2 | 0.5 | | |
| 210 | Not assigned | 2.8 | 1.9 | | |
| 232 | $(C_6F_5)C_5H_5$ | <1 | | | |
| 274 | $(C_6F_5)(nPr)C_5H_4$ | 2.3 | 2.1 | 2.2 | 1.4 |
| 304 | $(Me_3Si)(C_6F_5)C_5H_4$ | 2.7 | 2.7 | 2.6 | 1.9 |
| 274 | $(C_6F_5)(nPr)C_5H_4$ | <1 | | 1.3 | 0.8 |
| 398 | $(C_6F_5)_2Cp$ | <1 | | | |
| 346 | 1,3,4-$(SiMe_3)(C_6F_5)$(n-Pr)$C_5H_3$ | 47.6 | 54.8 | 52.7 | 43.3 |
| 346 | 1,3,5-$(SiMe_3)(C_6F_5)$(n-Pr)$C_5H_3$ | 13.4 | 15.4 | 15.0 | 12.3 |
| 376 | $(SiMe_3)_2(C_6F_5)C_5H_3$ | 9.1 | 11.4 | 10.0 | 9.0 |
| 388 | $(SiMe_3)(C_6F_5)$(n-Pr)$_2C_5H_2$ | 8.5 | 11.0 | 9.3 | 8.6 |

TABLE 6-continued

Analysis (GCMS) of Crude Product after Filtration Work-Up and after Distillation

| m/z (FW) | Assignment | Crude product after filtration work-up; 110.7 g | | Distilled product; 83.8 g | |
|---|---|---|---|---|---|
| | | GC area % (mol %) | Calcd. wt. of products (g) | GC area % (mol %) | Calcd. wt. of products (g) |
| 388 | $(SiMe_3)(C_6F_5)(n-Pr)_2C_5H_2$ | 6.2 | 8.0 | 6.9 | 6.4 |
| | Yield of regioisomeric $(SiMe_3)(C_6F_5)(n-Pr)C_5H_3$ species | 70.2 g/41% | | 55.6 g/32% | |
| | Yield of 1,3,4-$(SiMe_3)(C_6F_5)(n-Pr)C_5H_3$ | 54.8 g/32% | | 43.3 g/25% (based on 500 mmol $C_6F_6$) | |
| | Ratio of 1,3,4/1,3,5 regioisomers | 3.6:1 | | 3.5:1 | |

Example 8

Preparation of $(1,2-(C_6F_5)(n-Pr)C_5H_3)TiCl_3$ Using Neat Ligand

To neat 1,3,4-$(SiMe_3)(C_6F_5)(n-Pr)C_5H_3$ (95.6 g, 57% purity, 157 mmol) heated at 60° C. was added $TiCl_4$ (35.8 g, 189 mmol) in ~2 minutes. The mixture was stirred for an additional 3 hours after which the volatiles were removed at 60° C., ~1000 mTorr. Pentane (200 mL) was added and the resulting solution cooled to −35° C. overnight. The precipitated yellow solids were separated by filtration and the residue washed with pentane (3×25 mL) to afford 47.6 g of $(1,2-(C_6F_5)(n-Pr)C_5H_3)TiCl_3$ (77% yield based on estimated amount of ligand).

Example 9

Preparation of $(1,2-(C_6F_5)(n-Pr)C_5H_3)TiCl_3$ Using Solvated Ligand

To a stirred solution of 1,3,4-$(SiMe_3)(C_6F_5)(n-Pr)C_5H_3$ (36.4 g, 59% purity, 62 mmol) in heptane (30 mL) was added $TiCl_4$ (14.43 g, 76 mmol) and the reaction mixture was heated at 90° C. for 5 h. The reaction mixture was allowed to cool and an additional 25 mL of heptane was added. The product precipitated and was isolated by filtration. The filter cake was washed with pentane (3×25 mL) to give $(1,2-(C_6F_5)(n-Pr)C_5H_3)TiCl_3$ as a bright orange solid (18.8 g, 71% yield, based on the estimated amount of pure ligand).

Example 10

Preparation of $(1,2-(C_6F_5)(n-Pr)C_5H_3)(t-Bu_3P=N)TiCl_2$

Toluene (250 mL) was added to a mixture of solid $(1,2-(C_6F_5)(n-Pr)C_5H_3)TiCl_3$ (81.98 g, 191.8 mmol) and $t-Bu_3PNSiMe_3$ (55.74 g, 191.8 mmol). The reaction mixture was heated at 80° C. for 3 h and then about 20 mL of volatiles were removed resulting in the precipitation of the target compound. The precipitated solid, $(1,2-(C_6F_5)(n-Pr)C_5H_3)(t-Bu_3PN)TiCl_2$, was separated by filtration and the filter cake was washed with pentane (3×25 mL) and then dried under vacuum to afford 113.9 g (97.6% yield).

What is claimed is:

1. A method for making the compound 1,3,4-$(SiMe_3)(C_6F_5)(R)C_5H_3$ without isolating intermediates, said method comprising the following steps:

Step 1) in the presence of an ethereal solvent, combining perfluorobenzene $C_6F_6$, a metal cyclopentadienide $[M^1][C_5H_5]$ and a first base $M^2B^1$ to form a first reaction mixture comprising $[M^1/M^2][(C_6F_5)C_5H_4]$;

Step 2) combining at least 2 molar equivalents of $ClSiMe_3$ with said first reaction mixture to give a second reaction mixture comprising 1,3-$(SiMe_3)(C_6F_5)C_5H_4$;

Step 3) combining a second base $M^3B^2$ with said second reaction mixture to give a third reaction mixture comprising $[M^1/M^2/M^3][1,3-(SiMe_3)(C_6F_5)C_5H_3]$;

Step 4) combining a compound RX with said third mixture to give a fourth reaction mixture comprising 1,3,4-$(SiMe_3)(C_6F_5)(R)C_5H_3$;

wherein $M^1$, $M^2$, $M^3$ are the same or different metal selected from the group consisting of $Li^+$, $Na^+$ and $K^+$; $B^1$ and $B^2$ are the same or different base selected from the group consisting of hydride, alkylide, amide and alkoxide; R is a primary or secondary alkyl group which may be substituted by one or more heteroatom or heteroatom group; and X is a halide group or a sulfonate group.

2. The method of claim 1 wherein approximately equimolar amounts of $C_6F_6$, $[Na][C_5H_5]$ and NaH are combined in step 1.

3. The method of claim 1 wherein $C_6F_6$ is combined with approximately 2 molar equivalents of $[Na][C_5H_5]$ in step 1.

4. The method of claim 1 wherein $C_6F_6$ is added slowly over at least 30 min to approximately 2 molar equivalents of $[Na][C_5H_5]$ in step 1.

5. The method of claim 1 wherein $C_6F_6$ is added slowly over at least 30 min to an approximately equimolar amount of a 1:1 mixture of $[Na][C_5H_5]$ and NaH in step 1.

6. The method of claim 1 wherein approximately 2 molar equivalents of $ClSiMe_3$ are combined with the first reaction mixture in step 2.

7. The method of claim 1 wherein the first reaction mixture is added to approximately 2 molar equivalents of $ClSiMe_3$ in step 2.

8. The method of claim 1 wherein approximately 2 molar equivalents of $ClSiMe_3$ are added in less than 5 min to the first reaction mixture in step 2.

9. The method of claim 1 wherein approximately 1 molar equivalent of the second base $M^3B^2$ is combined with the second reaction mixture in step 3.

10. The method of claim 8 wherein approximately 1 molar equivalent of the second base $M^3B^2$ is added to the second reaction mixture in step 3.

11. The method of claim 1 wherein the second base $M^3B^2$ is selected from the group consisting of [Na][O-tBu] and [K][O-tBu].

12. The method of claim 1 wherein the second base $M^3B^2$ is a metal alkylide reagent.

13. The method of claim 12 wherein the metal alkylide reagent is n-butyllithium.

14. The method of claim 12 wherein the metal alkylide reagent is $[Na][C_5H_5]$.

15. The method of claim 1 wherein at least 1 molar equivalent of RX is combined with the third reaction mixture comprising $[M^1/M^2/M^3][1,3-(SiMe_3)(C_6F_5)C_5H_3]$ in step 4.

16. The method of claim 1 wherein approximately 1.5 molar equivalents of RX are combined with the third reaction mixture comprising $[M^1/M^2/M^3][1,3-(SiMe_3)(C_6F_5)C_5H_3]$ in step 4.

17. The method of claim 10 wherein at least 1 molar equivalent of RX is added to the third reaction mixture comprising $[M^1/M^2/M^3][1,3-(SiMe_3)(C_6F_5)C_5H_3]$ in step 4.

18. The method of claim 17 wherein steps 1-4 are carried out in a single reaction vessel.

19. The method of claim 1 wherein R is a primary or a secondary alkyl group which is substituted by one or more heteroatom or heteroatom containing group.

20. The method of claim 1 wherein R is a primary alkyl group which is substituted by one or more fluoride atom.

21. The method of claim 1 wherein the compound RX is a primary alkyl halide in which R is a primary alkyl group and X is Cl, Br or I.

22. The method of claim 1 wherein the compound RX is a primary alkyl halide in which R is a primary alkyl group which is substituted by one or more fluoride atom and X is Cl, Br or I.

23. The method of claim 1 wherein the compound RX is a primary alkyl halide which is selected from the group consisting of n-propyl bromide, n-butyl bromide, n-pentyl bromide, n-hexyl bromide, benzyl bromide and perfluorophenylbenzyl bromide.

24. The method of claim 1 wherein the ethereal solvent is selected from the group consisting of diethyl ether, diisopropyl ether, di-n-butyl ether, di-n-propyl ether, methyl t-butyl ether, diphenyl ether, tetrahydrofuran, 2-methyl-tetrahydrofuran or a mixture thereof.

25. The method of claim 1 wherein the ethereal solvent is selected from diethyl ether, tetrahydrofuran or a mixture thereof.

26. The method of claim 1 wherein the ethereal solvent is tetrahydrofuran.

27. The method of claim 26 wherein the tetrahydrofuran has less than 20 ppm of water.

28. The method of claim 1 wherein the compound 1,3,4-$(SiMe_3)(C_6F_5)(R)C_5H_3$ is prepared at a 500 mmol scale or higher.

29. The method of claim 1 further comprising:
a) removing volatiles from the fourth reaction mixture under vacuum to give a first residue comprising 1,3,4-$(SiMe_3)(C_6F_5)(R)C_5H_3$;
b) diluting the first residue with a hydrocarbon solvent to give a hydrocarbon solution comprising 1,3,4-$(SiMe_3)(C_6F_5)(R)C_5H_3$;
c) extracting the hydrocarbon solution with a mildly acidic aqueous solution to at least partially remove inorganic salts from the hydrocarbon solution comprising 1,3,4-$(SiMe_3)(C_6F_5)(R)C_5H_3$;
d) removing volatiles from the hydrocarbon solution under vacuum to give a crude product comprising 1,3,4-$(SiMe_3)(C_6F_5)(R)C_5H_3$ as the majority species by weight.

30. The method of claim 1 further comprising:
a) diluting the fourth mixture with a hydrocarbon solvent to give a product mixture comprising 1,3,4-$(SiMe_3)(C_6F_5)(R)C_5H_3$;
b) extracting the product mixture with a mildly acidic aqueous solution to at least partially remove inorganic salts from the product mixture comprising 1,3,4-$(SiMe_3)(C_6F_5)(R)C_5H_3$;
c) removing volatiles from the product mixture under vacuum to give a crude product comprising 1,3,4-$(SiMe_3)(C_6F_5)(R)C_5H_3$ as the majority species by weight.

31. The method of claim 1, further comprising:
a) removing volatiles from the fourth reaction mixture under vacuum to give a first residue comprising 1,3,4-$(SiMe_3)(C_6F_5)(R)C_5H_3$;
b) extracting the first residue with a hydrocarbon solvent to give a hydrocarbon solution comprising 1,3,4-$(SiMe_3)(C_6F_5)(R)C_5H_3$;
c) filtering the hydrocarbon solution comprising 1,3,4-$(SiMe_3)(C_6F_5)(R)C_5H_3$ to give a filtrate comprising 1,3,4-$(SiMe_3)(C_6F_5)(R)C_5H_3$;
b) removing volatiles from the filtrate to give a crude product comprising 1,3,4-$(SiMe_3)(C_6F_5)(R)C_5H_3$ as the majority species by weight.

32. The method of claim 29, 30, or 31, further comprising vacuum distillation of the crude product to give a distillate comprising 1,3,4-$(SiMe_3)(C_6F_5)(R)C_5H_3$ in at least 40% purity by mole.

33. A method for making the compound 1,3,4-$(SiMe_3)(C_6F_5)(R)C_5H_3$ in a single reaction vessel without isolating intermediates, said method comprising the following steps:
Step 1) in the presence of an ethereal solvent, combining perfluorobenzene $C_6F_6$, a metal cyclopentadienide $[M1C_5H_5]$ and a first base $M^213^1$ to form a first reaction mixture comprising $[M^1/M^2][(C_6F_5)C_5H_4]$;
Step 2) adding at least 2 equivalents of $ClSiMe_3$ to said first reaction mixture to give a second reaction mixture comprising 1,3-$(SiMe_3)(C_6F_5)C_5H_4$;
Step 3) adding a second base $M^3B^2$ to said second reaction mixture to give a third reaction mixture comprising $[M^1/M^2/M^3][1,3-(SiMe_3)(C_6F_5)C_5H_3]$;
Step 4) adding an alkyl halide RX to said third mixture to give a fourth reaction mixture comprising 1,3,4-$(SiMe_3)(C_6F_5)(R)C_5H_3$;
wherein $M^1$, $M^2$, $M^3$ are the same or different metals selected from the group comprising $Li^+$, $Na^+$ and $K^+$; $B^1$ and $B^2$ are the same or different bases selected from the group comprising hydride, alkylide, amide and alkoxide; R is a primary or secondary alkyl group which may be substituted by one or more heteroatom or heteroatom group; and X is a halide group or a sulfonate group.

34. The method of claim 33 wherein R is a primary or a secondary alkyl group which is substituted by one or more heteroatom or heteroatom containing group.

35. The method of claim 33 wherein R is a primary alkyl group which is substituted by one or more fluoride atom.

36. The method of claim 33 wherein the compound RX is a primary alkyl halide in which R is a primary alkyl group and X is Cl, Br or I.

37. The method of claim 33 wherein the compound RX is a primary alkyl halide in which R is a primary alkyl group which is substituted by one or more fluoride atom and X is Cl, Br or I.

38. The method of claim 33 wherein the compound RX is a primary alkyl halide which is selected from the group consisting of n-propyl bromide, n-butyl bromide, n-pentyl bromide, n hexyl bromide, benzyl bromide and perfluorophenyl-benzyl bromide.

\* \* \* \* \*